(12) United States Patent
Lim et al.

(10) Patent No.: US 9,196,838 B2
(45) Date of Patent: Nov. 24, 2015

(54) ORGANIC COMPOUND AND ORGANIC LIGHT-EMITTING DEVICE COMPRISING THE SAME

(71) Applicant: Samsung Display Co., Ltd., Yongin, Gyeonggi-Do (KR)

(72) Inventors: Jin-O Lim, Yongin (KR); Seok-Hwan Hwang, Yongin (KR); Young-Kook Kim, Yongin (KR); Hye-Jin Jung, Yongin (KR); Sang-Hyun Han, Yongin (KR); Soo-Yon Kim, Yongin (KR); Eun-Jae Jeong, Yongin (KR); Jun-Ha Park, Yongin (KR); Eun-Young Lee, Yongin (KR); Il-Soo Oh, Yongin (KR); Jong-Hyuk Lee, Yongin (KR)

(73) Assignee: Samsung Display Co., Ltd., Samsung-ro, Giheung-Gu, Yongin-si, Gyeonggi-Do (KR)

( * ) Notice: Subject to any disclaimer, the term of this patent is extended or adjusted under 35 U.S.C. 154(b) by 182 days.

(21) Appl. No.: 13/944,003

(22) Filed: Jul. 17, 2013

(65) Prior Publication Data
US 2014/0117327 A1 May 1, 2014

(30) Foreign Application Priority Data

Oct. 30, 2012 (KR) ........................ 10-2012-0121527

(51) Int. Cl.
*H01L 35/24* (2006.01)
*H01L 51/00* (2006.01)
(Continued)

(52) U.S. Cl.
CPC .......... *H01L 51/0054* (2013.01); *C07B 59/001* (2013.01); *C07C 13/00* (2013.01); *C07C 13/66* (2013.01); *C07C 15/38* (2013.01); *C07C 25/22* (2013.01); *C07C 43/2055* (2013.01); *C07C 255/51* (2013.01); *C07C 381/12* (2013.01); *C07D 209/86* (2013.01);
(Continued)

(58) Field of Classification Search
CPC ............ H01L 51/0541; H01L 51/0545; H01L 51/0036; H01L 51/5012; H01L 51/0054
USPC ............................................ 257/40, E51.001
See application file for complete search history.

(56) References Cited

U.S. PATENT DOCUMENTS

| 5,635,308 A | 6/1997 | Inoue et al. |
| 5,972,247 A | 10/1999 | Shi et al. |

(Continued)

FOREIGN PATENT DOCUMENTS

| JP | 8-12600 | 1/1996 |
| JP | 2000-003782 | 1/2000 |

(Continued)

*Primary Examiner* — Anthony Ho
(74) *Attorney, Agent, or Firm* — Robert E. Bushnell, Esq.

(57) ABSTRACT

An organic compound represented by Formula 1 below and an organic light-emitting device including the organic compound;

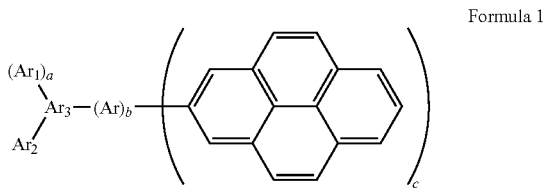

Formula 1

Wherein $Ar_1$, $Ar_2$, $Ar_3$, $Ar_4$, a, b, and c are defined as in the specification.

18 Claims, 1 Drawing Sheet

(51) Int. Cl.

| | | |
|---|---|---|
| *C07C 13/00* | (2006.01) | |
| *C07C 13/66* | (2006.01) | |
| *C07C 15/38* | (2006.01) | |
| *C07C 25/22* | (2006.01) | |
| *C07C 255/51* | (2006.01) | |
| *C07C 381/12* | (2006.01) | |
| *C07C 43/205* | (2006.01) | |
| *C07B 59/00* | (2006.01) | |
| *C07D 333/76* | (2006.01) | |
| *C07D 209/86* | (2006.01) | |
| *C07D 307/91* | (2006.01) | |
| *C07F 7/08* | (2006.01) | |
| *H01L 51/50* | (2006.01) | |

(52) U.S. Cl.
CPC ........... *C07D 307/91* (2013.01); *C07D 333/76* (2013.01); *C07F 7/0809* (2013.01); *H01L 51/0058* (2013.01); *H01L 51/0073* (2013.01); *H01L 51/0074* (2013.01); *C07C 2103/18* (2013.01); *C07C 2103/24* (2013.01); *C07C 2103/50* (2013.01); *H01L 51/0081* (2013.01); *H01L 51/5012* (2013.01)

(56) References Cited

U.S. PATENT DOCUMENTS

| | | | |
|---|---|---|---|
| 6,465,115 | B2 | 10/2002 | Shi et al. |
| 6,596,415 | B2 | 7/2003 | Shi et al. |
| 7,854,999 | B2 | 12/2010 | Park et al. |
| 7,875,367 | B2 | 1/2011 | Park et al. |
| 2007/0290610 | A1 | 12/2007 | Park et al. |

FOREIGN PATENT DOCUMENTS

| | | |
|---|---|---|
| JP | 2009-096771 | 5/2009 |
| KR | 10-2007-0119470 A | 12/2007 |
| KR | 10-2008-0030260 A | 4/2008 |
| KR | 10-2008-0039057 A | 5/2008 |

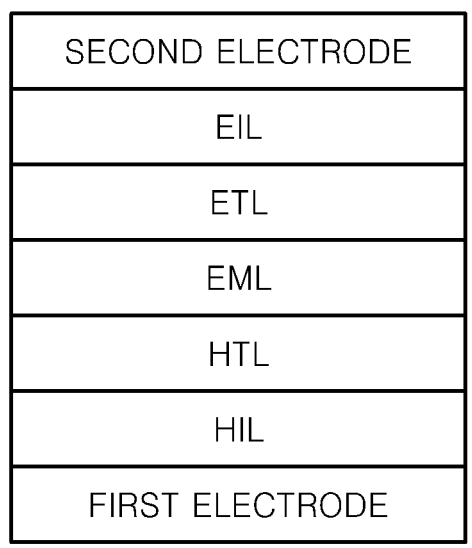

ORGANIC COMPOUND AND ORGANIC LIGHT-EMITTING DEVICE COMPRISING THE SAME

CLAIM OF PRIORITY

This application makes reference to, incorporates the same herein, and claims all benefits accruing under 35 U.S.C. §119 from an application for ORGANIC COMPOUND AND ORGANIC LIGHT-EMITTING DEVICE INCLUDING THE SAME, earlier filed in the Korean Intellectual Property Office on Oct. 30, 2012 and there duly assigned Serial No. 10-2012-0121527.

BACKGROUND OF THE INVENTION

1. Field of the Invention

The present invention relates to an organic compound and an organic light-emitting device including the organic compound.

2. Description of the Related Art

Organic light-emitting devices (OLEDs), which are self-emitting devices, have advantages such as wide viewing angles, excellent contrast, quick response, high brightness, excellent driving voltage characteristics, and can provide multicolored images.

A typical OLED has a structure including a substrate, and an anode, a hole transport layer (HTL), an emission layer (EML), an electron transport layer (ETL), and a cathode which are sequentially stacked on the substrate. In this regard, the HTL, the EML, and the ETL are organic thin films formed of organic compounds.

An operating principle of an OLED having the above-described structure is as follows.

When a voltage is applied between the anode and the cathode, holes injected from the anode move to the EML via the HTL, and electrons injected from the cathode move to the EML via the ETL. The holes and electrons recombine in the EML to generate excitons. When the excitons drop from an excited state to a ground state, light is emitted.

There is an ongoing demand for a material having improved electrical stability, high charge-transfer or emission capability, and a high glass transition temperature that is high enough to prevent crystallization, in regards to existing unimolecular materials.

SUMMARY OF THE INVENTION

The present invention provides a novel organic compound with improved characteristics, and a high-efficiency, low-voltage, high-luminance, and long-lifetime organic light-emitting device including the novel compound.

The novel organic compound has improved electrical characteristics, good charge transporting capabilities, improved emission capability, a high glass transition temperature (Tg) enough to prevent crystallization. The novel organic compound is suitable as a light-emitting material for fluorescent or phosphorescent device of any color of red, green, blue, or white.

According to an aspect of the present invention, there is provided an organic compound represented by Formula 1 below:

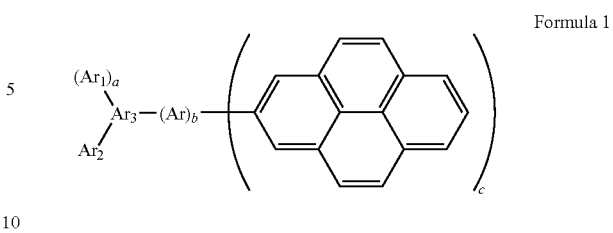

Formula 1 wherein, in Formula 1, $Ar_1$, $Ar_2$, $Ar_3$, and $Ar_4$ may be each independently a substituted or unsubstituted $C_6$-$C_{60}$ aryl group, a substituted or unsubstituted $C_{10}$-$C_{60}$ condensed polycyclic group, or a substituted or unsubstituted $C_3$-$C_{60}$ heteroaryl group; a may be an integer from 0 to 2; b may be an integer from 0 to 4; and c may be an integer from 1 to 3, wherein b may be optionally at least two, and the two or more $Ar_4$s may be identical to or differ from each other.

According to another aspect of the present invention, there is provided an organic light-emitting device including a first electrode, a second electrode, and an organic layer disposed between the first electrode and the second electrode, wherein the organic layer includes the organic compound of Formula 1 described above.

According to another aspect of the present invention, there is provided a flat panel display device including the above-described organic light-emitting device, wherein the first electrode of the organic light-emitting device is electrically connected to a source electrode or a drain electrode of a thin-film transistor.

BRIEF DESCRIPTION OF THE DRAWINGS

A more complete appreciation of the present invention, and many of the attendant advantages thereof, will be readily apparent as the present invention becomes better understood by reference to the following detailed description when considered in conjunction with the accompanying drawings in which like reference symbols indicate the same or similar components, wherein FIG. 1 schematically illustrates a structure of an organic light-emitting device according to an embodiment of the present invention.

DETAILED DESCRIPTION OF THE INVENTION

The present invention will be described more fully with reference to the accompanying drawings, in which exemplary embodiments of the present invention are shown.

As used herein, the term "and/or" includes any and all combinations of one or more of the associated listed items. Expressions such as "at least one of," when preceding a list of elements, modify the entire list of elements and do not modify the individual elements of the list.

According to an aspect of the present invention, there is provided an organic compound represented by Formula 1 below.

Formula 1

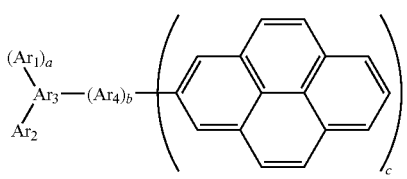

In Formula 1, $Ar_1$, $Ar_2$, $Ar_3$, and $Ar_4$ may be each independently a substituted or unsubstituted $C_6$-$C_{60}$ aryl group, a substituted or unsubstituted $C_{10}$-$C_{60}$ condensed polycyclic group, or a substituted or unsubstituted $C_3$-$C_{60}$ heteroaryl group; a may be an integer from 0 to 2; b may be an integer from 0 to 4; and c may be an integer from 1 to 3, wherein b may be optionally at least two, and the two or more $Ar_4$s may be identical to or differ from each other.

The organic compound of Formula 1 above may be used as a light-emitting material for organic light-emitting devices. The organic compound of Formula 1 may have a high glass transition temperature (Tg) or melting point. Thus, the organic compound has high heat resistance against Joule's heat generated in an organic layer, between organic layers, or between an organic layer and a metal electrode when light emission occurs, and has high durability in high-temperature environments. An organic light-emitting device manufactured using the organic compound of Formula 1 has high durability when stored or operated.

Substituents in the organic compound of Formula 1 will now be described in detail.

In some embodiments of the present invention, in Formula 1, $Ar_1$ and $Ar_2$ may be each independently a group represented by one of Formulae 2a to 2e.

2a
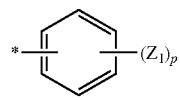

2b
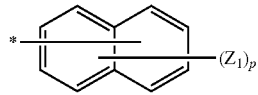

2c
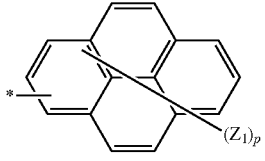

2d
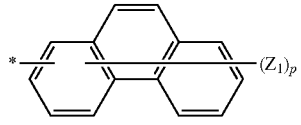

2e
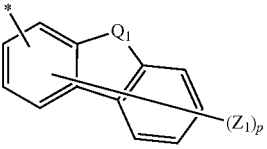

In Formulae 2a to 2e, $Q_1$ may be a linker represented by —$C(R_{30})(R_{31})$—, —$N(R_{32})$—, —S—, or —O—; $Z_1$, $R_{30}$, $R_{31}$, and $R_{32}$ may be each independently hydrogen, deuterium, a substituted or unsubstituted $C_1$-$C_{20}$ alkyl group, a substituted or unsubstituted $C_5$-$C_{20}$ aryl group, a substituted or unsubstituted $C_3$-$C_{20}$ heteroaryl group, a substituted or unsubstituted $C_6$-$C_{20}$ condensed polycyclic group, —$Si(R_{40})_3$, a halogen group, a cyano group, a nitro group, a hydroxy group, or a carboxy group; $R_{40}$ may be a substituted or unsubstituted $C_1$-$C_{20}$ alkyl group, a substituted or unsubstituted $C_5$-$C_{20}$ aryl group, a substituted or unsubstituted $C_3$-$C_{20}$ heteroaryl group, or a substituted or unsubstituted $C_6$-$C_{20}$ condensed polycyclic group; p may be an integer from 1 to 9; and * may indicate a binding site.

In some other embodiments of the present invention, in Formula 1, $Ar_3$ may be a group represented by Formula 3a or Formula 3b.

3a
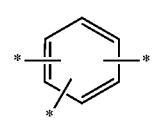

3b
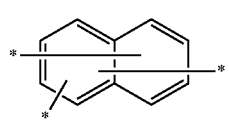

In Formula 3a and 3b, * may indicates a binding site.

In some other embodiments of the present invention, in Formula 1, $Ar_4$ may be a group represented by one of Formulae 4a to 4f.

4a
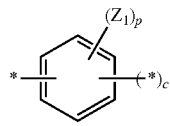

4b
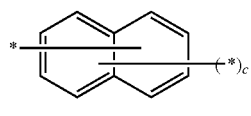

4c
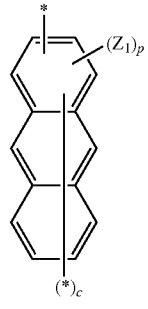

4d
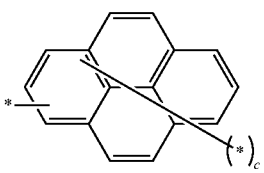

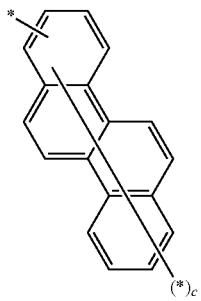

4e

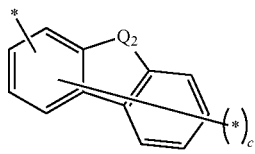

4f

In Formulae 4a to 4f, $Q_2$ may be a linker represented by —$C(R_{30})(R_{31})$—; $Z_1$, $R_{30}$, and $R_{31}$ may be each independently hydrogen, deuterium, a substituted or unsubstituted $C_1$-$C_{20}$ alkyl group, a substituted or unsubstituted $C_5$-$C_{20}$ aryl group, a substituted or unsubstituted $C_3$-$C_{20}$ heteroaryl group, a substituted or unsubstituted $C_6$-$C_{20}$ condensed polycyclic group, a halogen group, a cyano group, a nitro group, a hydroxyl group, or a carboxy group; and p may be an integer from 1 to 9; c may be an integer from 1 to 3; and * may indicate a binding site.

Hereinafter, substituents described with reference to the formulae will now be described in detail. In this regard, the numbers of carbons in substituents are presented only for illustrative purposes and do not limit the characteristics of the substituents.

The unsubstituted $C_1$-$C_{20}$ alkyl group used herein may be linear or branched. Examples of the alkyl group may include, but are not limited to, a methyl group, an ethyl group, a propyl group, an isobutyl group, a sec-butyl group, a pentyl group, an iso-amyl group, a hexyl group, a heptyl group, an octyl group, a nonanyl group, and a dodecyl group. At least one hydrogen atom of the alkyl group may be substituted with deuterium, a halogen atom, a hydroxyl group, a nitro group, a cyano group, an amino group, an amidino group, hydrazine, hydrazone, a carboxyl group or a salt thereof, a sulfonic acid group or a salt thereof, a phosphoric acid group or a salt thereof, a $C_1$-$C_{10}$ alkyl group, a $C_1$-$C_{10}$ alkoxy group, a $C_2$-$C_{10}$ alkenyl group, a $C_2$-$C_{10}$ alkynyl group, a $C_6$-$C_{16}$ aryl group, or a $C_4$-$C_{16}$ heteroaryl group.

The unsubstituted $C_5$-$C_{60}$ aryl group may indicate a carbocyclic aromatic system containing at least one ring. At least two rings may be fused to each other or linked to each other by a single bond. The term 'aryl' refers to an aromatic system, such as phenyl, naphthyl, or anthracenyl. At least one hydrogen atom in the aryl group may be substituted with a substituent described above in conjunction with the unsubstituted $C_1$-$C_{20}$ alkyl group.

Non-limiting examples of the substituted or unsubstituted $C_5$-$C_{60}$ aryl group may be a phenyl group, a $C_1$-$C_{10}$ alkylphenyl group (for example, ethylphenyl group), a halophenyl group (for example, o-, m-, and p-fluorophenyl group, dichlorophenyl group), a cyanophenyl group, dicyanophenyl group, a trifluoromethoxyphenyl group, a biphenyl group, a halobiphenyl group, a cyanobiphenyl group, a $C_1$-$C_{10}$ alkyl biphenyl group, a $C_1$-$C_{10}$ alkoxybiphenyl group, a o-, m-, and p-toryl group, an o-, m-, and p-cumenyl group, a mesityl group, a phenoxyphenyl group, a (α,α-dimethylbenzene) phenyl group, a (N,N'-dimethyl)aminophenyl group, a (N,N'-diphenyl)aminophenyl group, a pentalenyl group, an indenyl group, a naphthyl group, a halonaphthyl group (for example, fluoronaphthyl group), a $C_1$-$C_{10}$ alkylnaphthyl group (for example, methylnaphthyl group), a $C_1$-$C_{10}$ alkoxynaphthyl group (for example, methoxynaphthyl group), a cyanonaphthyl group, an anthracenyl group, an azulenyl group, a heptalenyl group, an acenaphthylenyl group, a phenalenyl group, a fluorenyl group, an anthraquinolyl group, a methylanthryl group, a phenanthryl group, a triphenylene group, a pyrenyl group, a chrycenyl group, an ethyl-chrysenyl group, a picenyl group, a perylenyl group, a chloroperylenyl group, a pentaphenyl group, a pentacenyl group, a tetraphenylenyl group, a hexaphenyl group, a hexacenyl group, a rubicenyl group, a coronelyl group, a trinaphthylenyl group, a heptaphenyl group, a heptacenyl group, a pyranthrenyl group, and an ovalenyl group.

The unsubstituted $C_3$-$C_{60}$ heteroaryl group used herein includes one, two or three hetero atoms selected from N, O, P and S. At least two rings may be fused to each other or linked to each other by a single bond. Non-limiting examples of the unsubstituted $C_3$-$C_{60}$ heteroaryl group may be a pyrazolyl group, an imidazolyl group, an oxazolyl group, a thiazolyl group, a triazolyl group, a tetrazolyl group, an oxadiazolyl group, a pyridinyl group, a pyridazinyl group, a pyrimidinyl group, a triazinyl group, a carbazol group, an indol group, a quinolyl group, an isoquinolyl group, and a dibenzothiophene group. In addition, at least one hydrogen atom in the heteroaryl group may be substituted with a substituent described above in conjunction with the unsubstituted $C_1$-$C_{20}$ alkyl group.

The unsubstituted $C_6$-$C_{60}$ condensed polycyclic group used herein refers to a substituent including at least two rings wherein at least one aromatic ring and/or at least one non-aromatic ring may be fused to each other, or refers to a substituent having an unsaturated group in a ring that may not form a conjugate structure. The unsubstituted $C_6$-$C_{60}$ condensed polycyclic group may be distinct from an aryl group or a heteroaryl group in terms of being non-aromatic.

Non-limiting examples of the organic compound of Formula 1 are Compounds 1 to 44 represented by the following formulae.

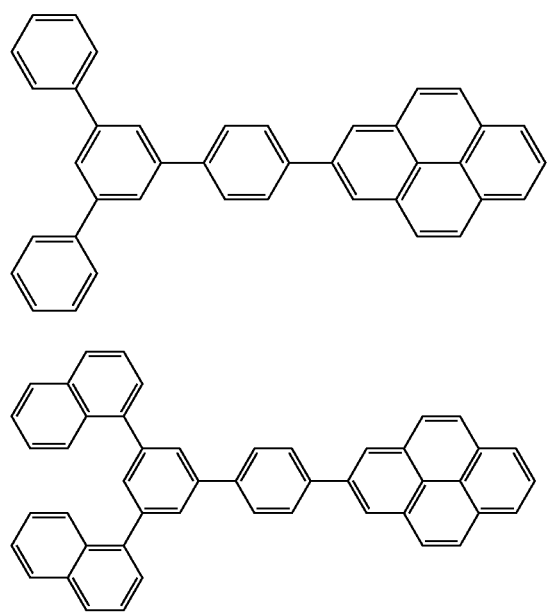
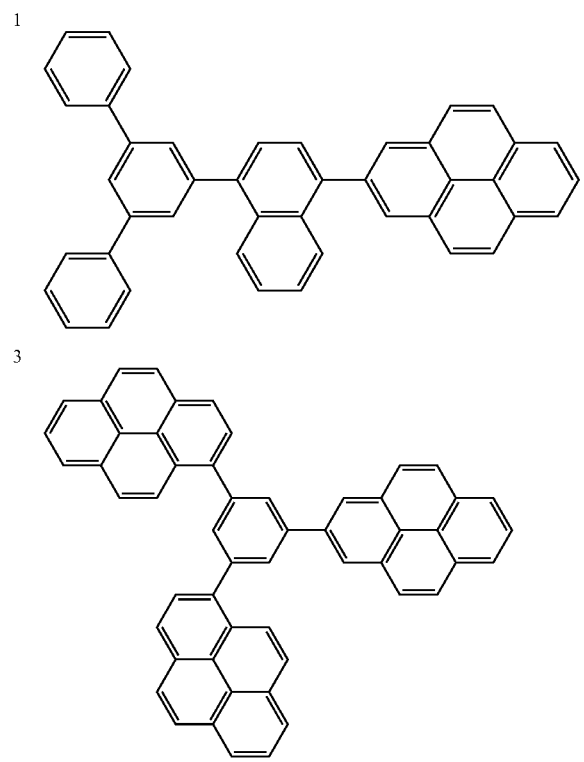
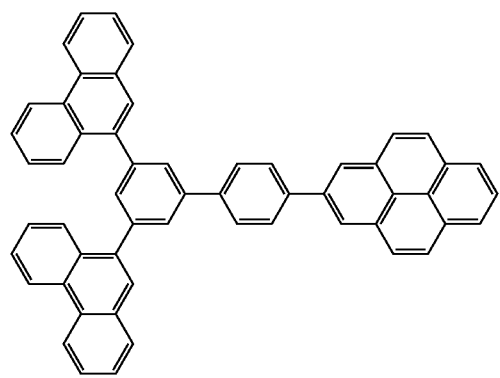
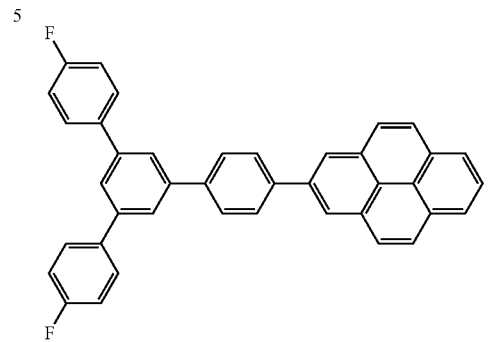
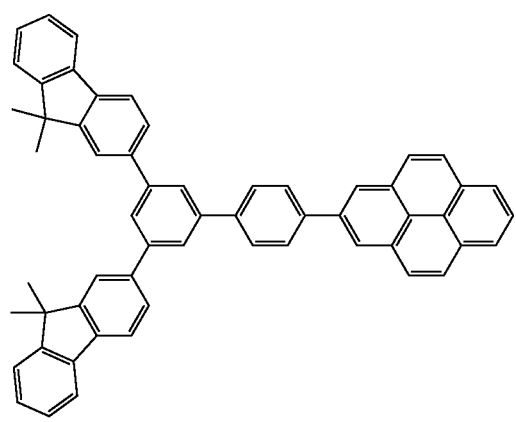
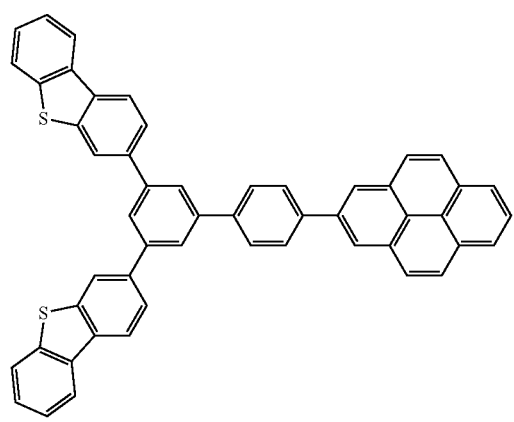

-continued
| | |
|---|---|
| 9 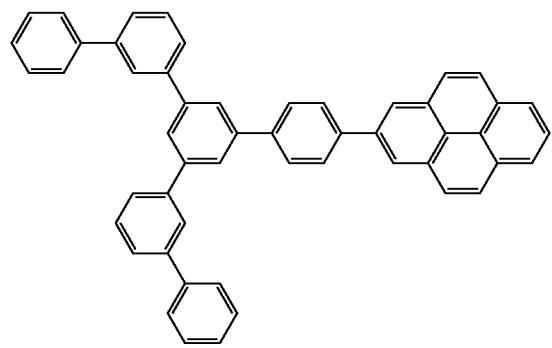 | 10 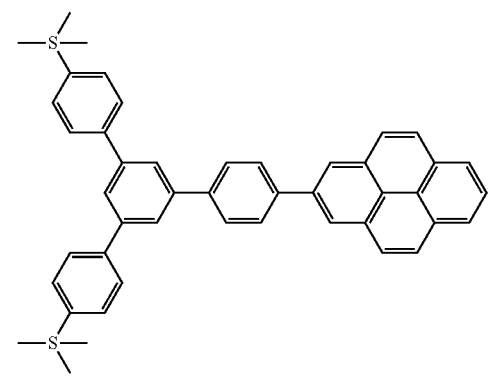 |
| 11 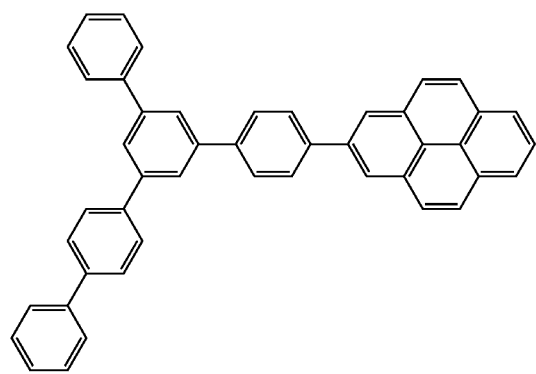 | 12 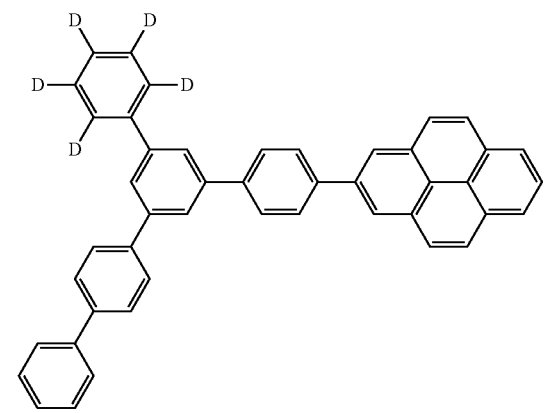 |
| 13 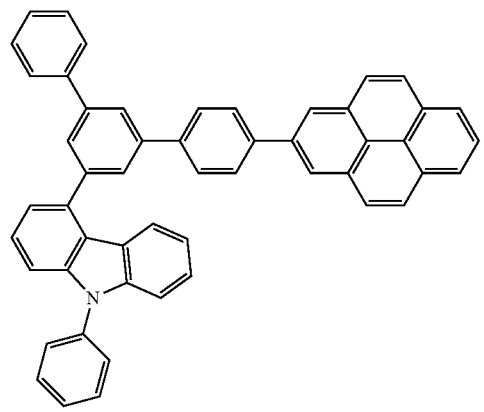 | 14 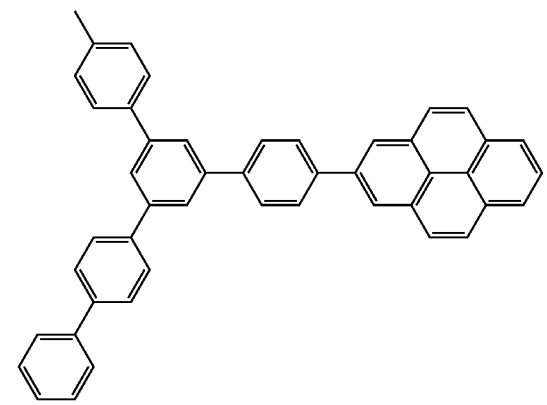 |
| 15 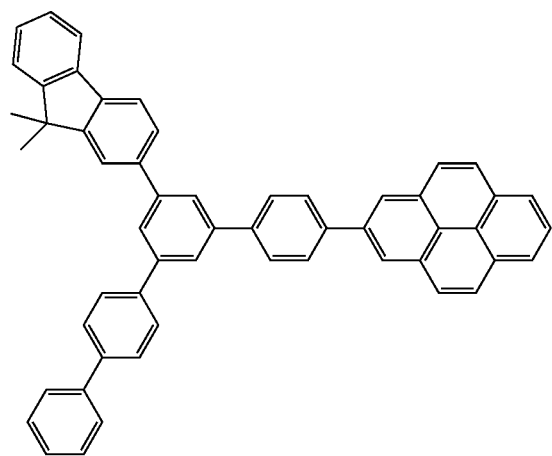 | 16 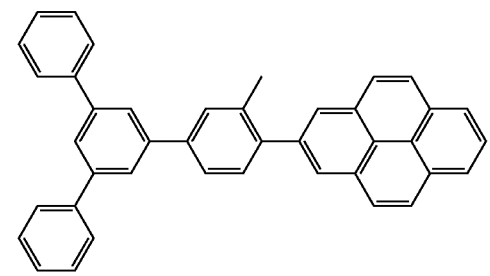 |

-continued
17
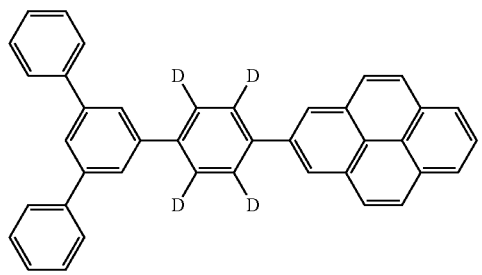
18
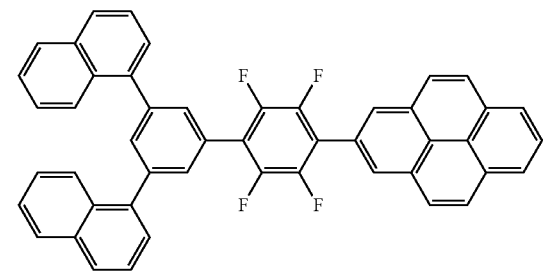
19
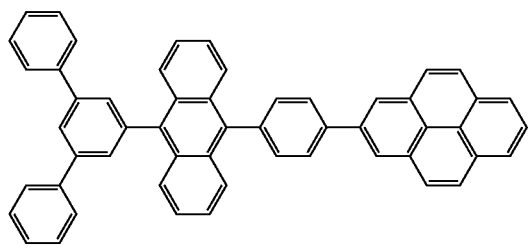
20
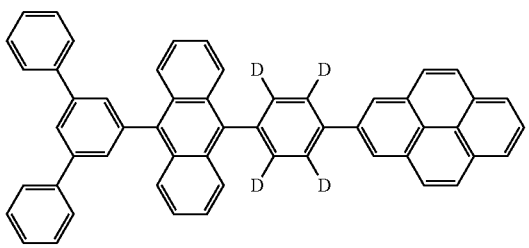
21
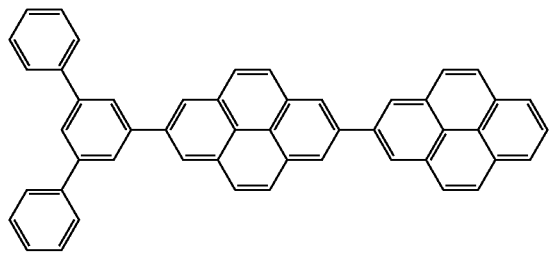
22
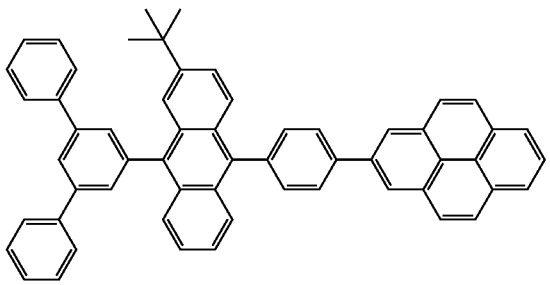
23
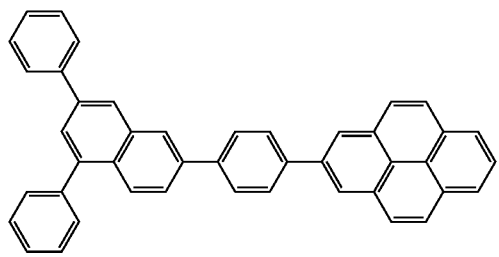
24
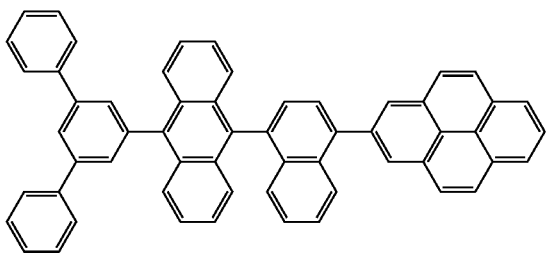
25
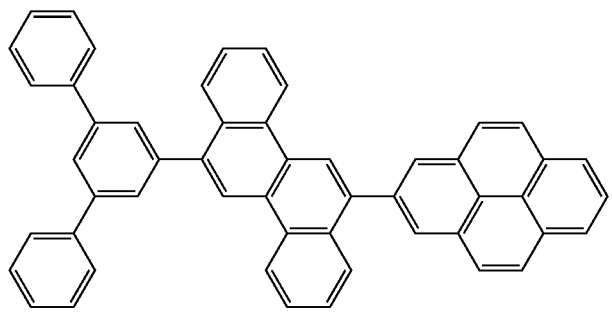

26
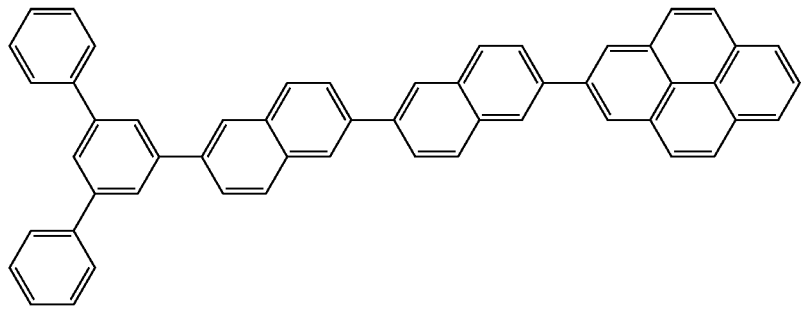
27
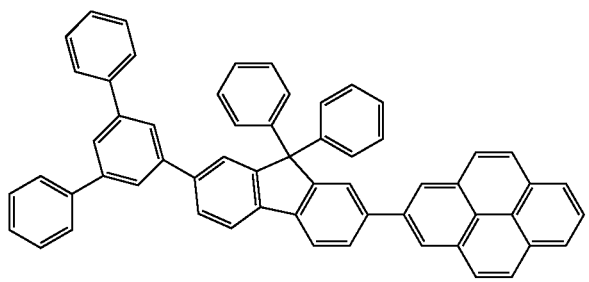
28
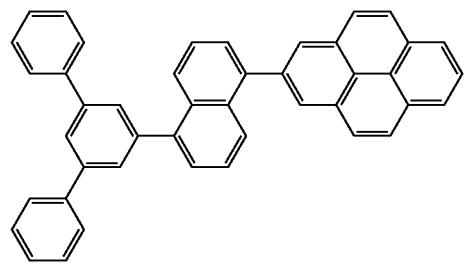
29
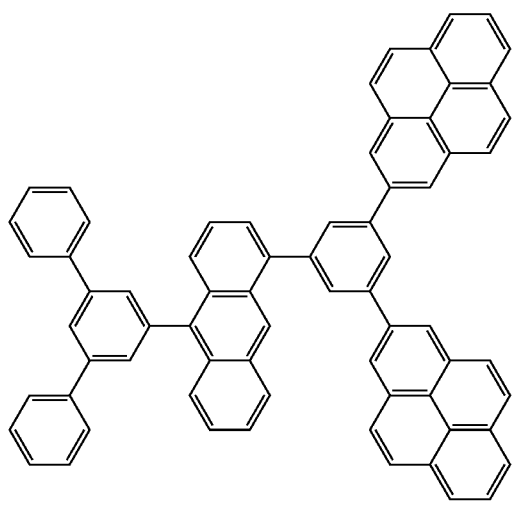
30
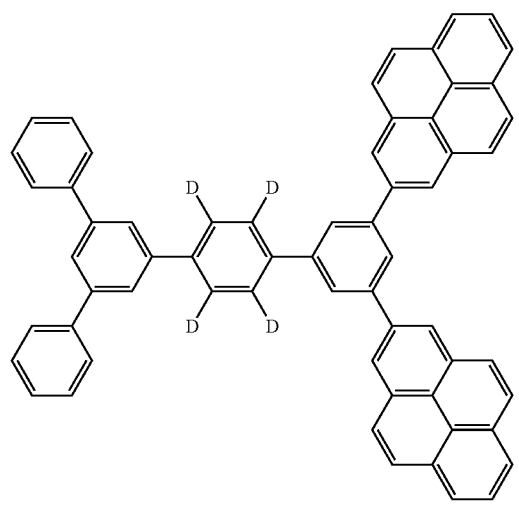
31
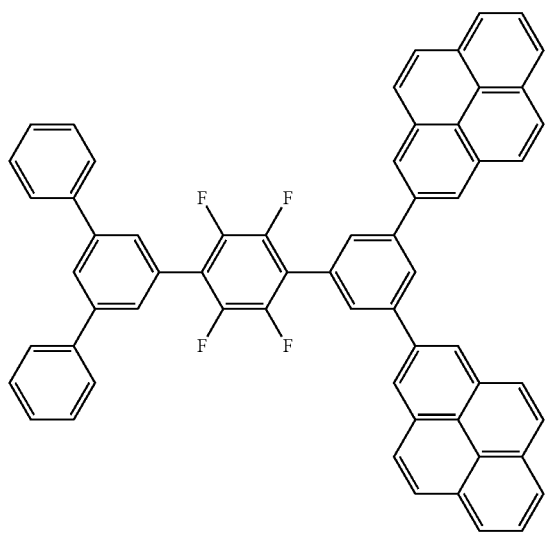
32
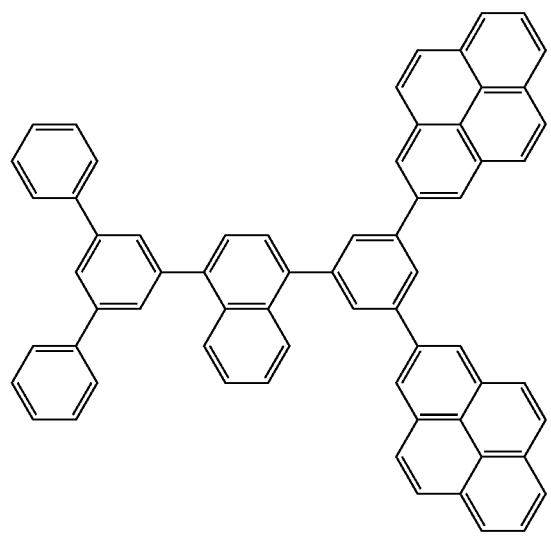

33
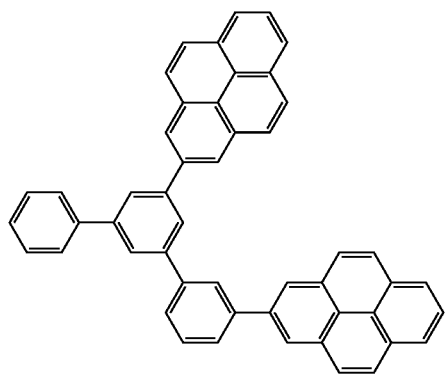
34
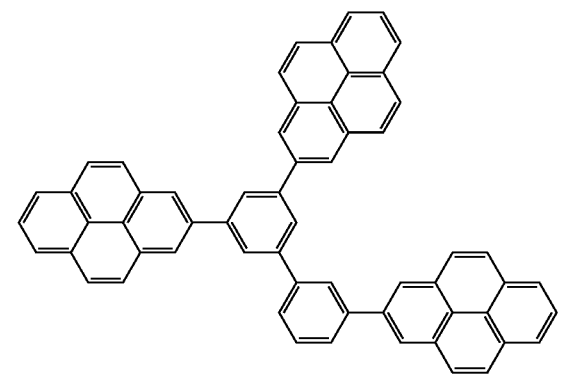
35
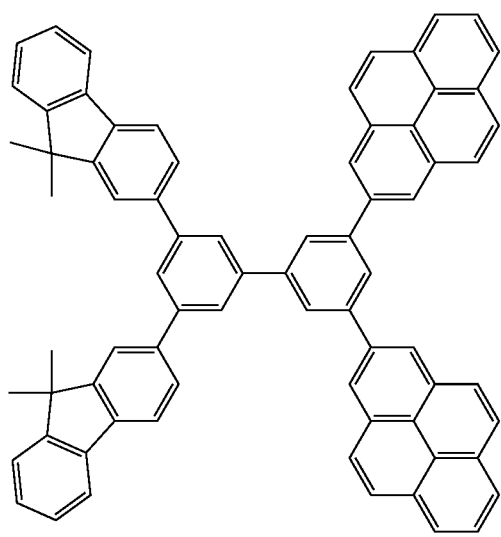
36
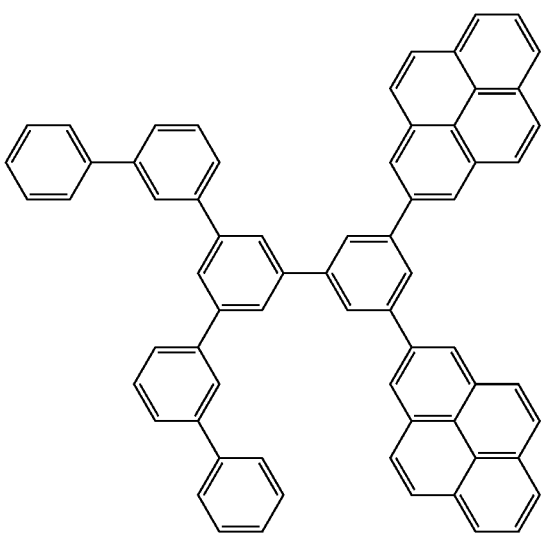
37
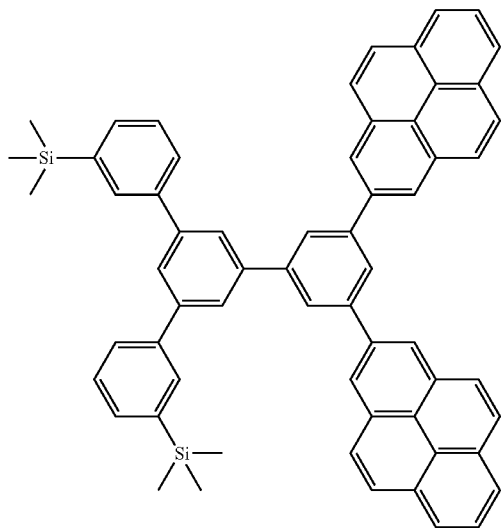
38
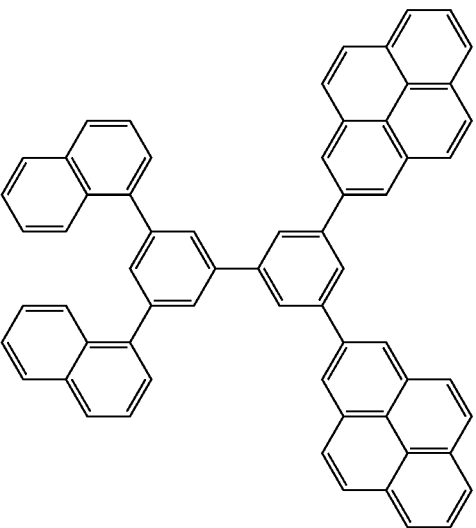

-continued

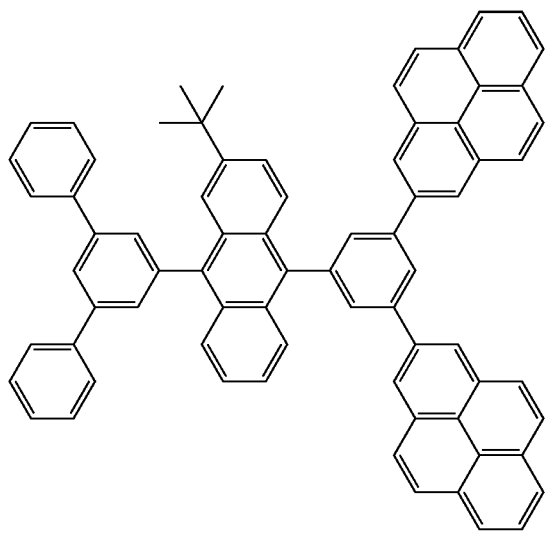

39

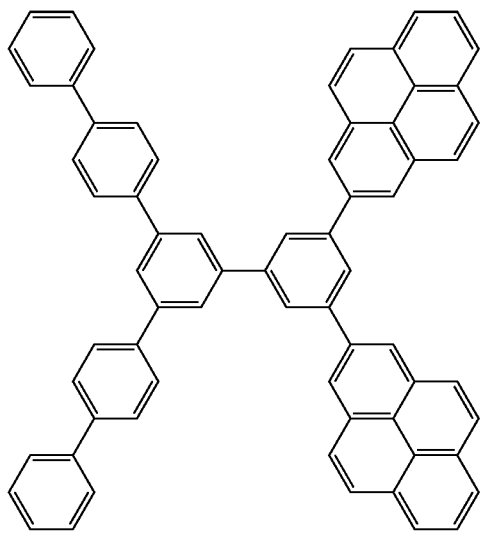

40

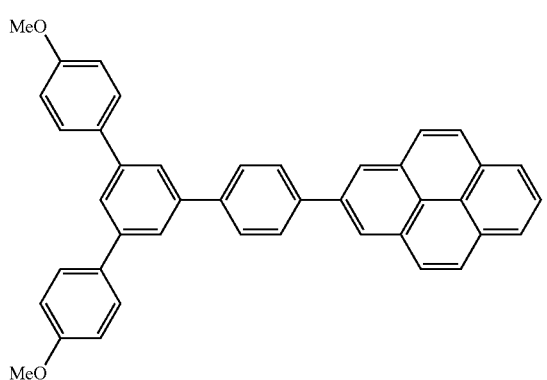

41

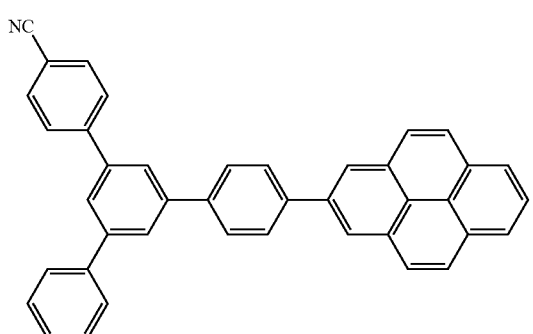

42

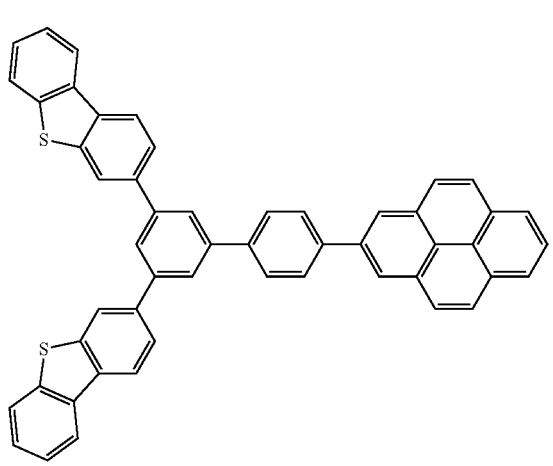

43

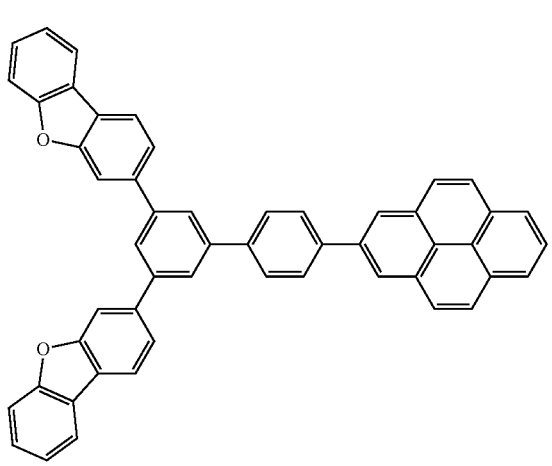

44

Another aspect of the present invention may provide an organic light-emitting device including a first electrode, a second electrode, and an organic layer disposed between the first electrode and the second electrode, wherein the organic layer includes the organic compound of Formula 1 described above.

The organic layer may include at least one layer selected from among a hole injection layer, a hole transport layer, a functional layer having both hole injection and hole transport capabilities (hereinafter, "H-functional layer"), a buffer layer, an electron blocking layer, an emission layer, a hole blocking layer, an electron transport layer, an electron injection layer, and a functional layer having both electron injection and electron transport capabilities (hereinafter, "E-functional layer").

The organic layer may be used as an emission layer. For example, the organic layer may be a blue emission layer.

In some embodiments of the present invention, the organic light-emitting device may include an electron injection layer, an electron transport layer, an emission layer, a hole injection layer, a hole transport layer, or a functional layer having both hole injection and transport capabilities; and the emission layer may include the organic compound of Formula 1 above, wherein the emission layer may further include an anthracene-based compound, an arylamine-based compound or a styryl-based compound.

In some other embodiments of the present invention, the organic light-emitting device may include an electron injection layer, an electron transport layer, an emission layer, a hole injection layer, a hole transport layer, or a functional layer having both hole injection and transport capabilities; and the emission layer may include the organic compound of Formula 1 above, and the emission layer may include a red emission layer, a green emission layer, a blue emission layer, and a white emission layer. At least one of the red emission layer, the green emission layer, the blue emission layer, and the white emission layer of the emission layer may include a phosphorescent compound; and at least one of the hole injection layer, the hole transport layer, and the functional layer having both hole injection and hole transport capabilities may include a charge-generating material.

In some embodiments of the present invention, the charge-generating material may be a p-type dopant, and the p-type dopant may be a quinine derivative, a metal oxide or a cyano group-containing compound.

In some embodiments of the present invention, the organic layer may include an electron transport layer, and the electron transport layer may include an electron-transporting organic compound and a metal complex. The metal complex may be a Li complex.

In some embodiments of the present invention, the metal complex may be lithium quinolate (LiQ), or Compound 203 below.

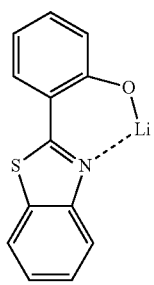

Compound 203

In some embodiments of the present invention, the organic layer may be formed from the organic compound of Formula 1 using a wet process.

Another aspect of the present invention may provide a flat panel display device comprising an organic light-emitting device as described above, and the first electrode of the organic light-emitting device is electrically connected to a source electrode or a drain electrode of a thin-film transistor.

The term "organic layer" as used herein refers to a single layer and/or a plurality of layers disposed between the first and second electrodes of the organic light-emitting device.

The organic layer may include an emission layer, and the emission layer may include the organic compound of Formula 1 described above. The organic layer may include at least one of a hole injection layer, a hole transport layer, and a functional layer having both hole injection and hole transport capabilities (hereinafter, "H-functional layer"); and at least one of the hole injection layer, the hole transport layer, and the functional layer having both hole injection and hole transport capabilities may include the organic compound of Formula 1.

FIG. 1 is a schematic sectional view of an organic light-emitting device according to an embodiment of the present invention. Hereinafter, a structure of an organic light-emitting device according to an embodiment of the present invention and a method of manufacturing the same will now be described with reference to FIG. 1.

A substrate (not shown) may be any substrate that is used in existing organic light emitting devices. In some embodiments the substrate may be a glass substrate or a transparent plastic substrate with strong mechanical strength, thermal stability, transparency, surface smoothness, ease of handling, and water resistance.

The first electrode may be formed by depositing or sputtering a first electrode-forming material on the substrate. When the first electrode is an anode, a material having a high work function may be used as the first electrode-forming material to facilitate hole injection. The first electrode may be a reflective electrode or a transmission electrode. Transparent and conductive materials such as ITO, IZO, $SnO_2$, and ZnO may be used to form the first electrode. The first electrode may be formed as a reflective electrode using magnesium (Mg), aluminum (Al), aluminum-lithium (Al—Li), calcium (Ca), magnesium-indium (Mg—In), magnesium-silver (Mg—Ag), or the like.

The first electrode may have a single-layer structure or a multi-layer structure including at least two layers. For example, the first electrode may have a three-layered structure of ITO/Ag/ITO, but is not limited thereto.

An organic layer(s) is disposed on the first electrode.

The organic layer may include a hole injection layer (HIL), a hole transport layer (HTL), a H-functional layer, a buffer layer (not shown), an emission layer (EML), an electron transport layer (ETL), or an electron injection layer (EIL).

The HIL may be formed on the first electrode by vacuum deposition, spin coating, casting, Langmuir-Blodgett (LB) deposition, or the like.

When the HIL is formed using vacuum deposition, vacuum deposition conditions may vary according to the compound that is used to form the HIL, and the desired structure and thermal properties of the HIL to be formed. For example, vacuum deposition may be performed at a temperature of about 100° C. to about 500° C., a pressure of about $10^{-8}$ torr to about $10^{-3}$ torr, and a deposition rate of about 0.01 to about 100 Å/sec. However, the deposition conditions are not limited thereto.

When the HIL is formed using spin coating, the coating conditions may vary according to the compound that is used to form the HIL, and the desired structure and thermal properties of the HIL to be formed. For example, the coating rate may be in the range of about 2000 rpm to about 5000 rpm, and a temperature at which heat treatment is performed to remove a solvent after coating may be in the range of about 80° C. to about 200° C. However, the coating conditions are not limited thereto.

The HIL may be formed of any material that is commonly used to form a HIL. Non-limiting examples of the material that can be used to form the HIL are N,N'-diphenyl-N,N'-bis-[4-(phenyl-m-tolyl-amino)-phenyl]-biphenyl-4,4'-diamine, (DNTPD), a phthalocyanine compound such as copperphthalocyanine, 4,4',4"-tris(3-methylphenylphenylamino)triphenylamine (m-MTDATA), N,N'-di(1-naphthyl)-N,N'-diphenylbenzidine (NPB), TDATA, 2-TNATA, polyaniline/dodecylbenzenesulfonic acid (Pani/DBSA), poly(3,4-ethylenedioxythiophene)/poly(4-styrenesulfonate) (PEDOT/PSS), polyaniline/camphorsulfonic acid (Pani/CSA), and polyaniline)/poly(4-styrenesulfonate) (PANI/PSS).

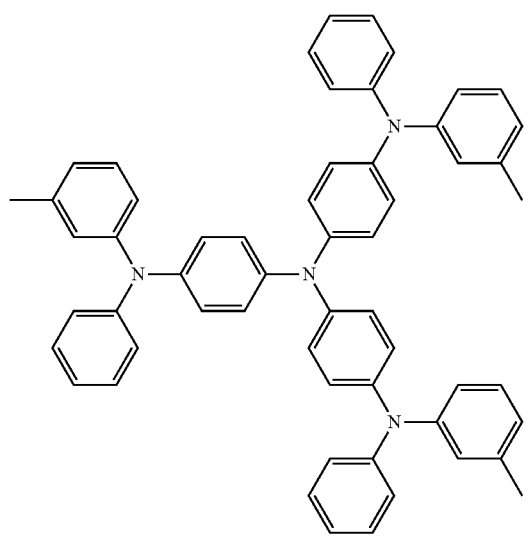

m-MTDATA

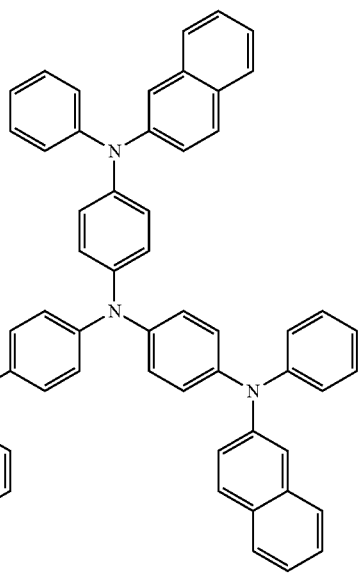

2-TNATA

The thickness of the HIL may be from about 100 Å to about 10000 Å, and in some embodiments, from about 100 Å to about 1000 Å. When the thickness of the HIL is within these ranges, the HIL may have good hole injecting ability without a substantial increase in driving voltage.

Then, a HTL may be formed on the HIL by using vacuum deposition, spin coating, casting, Langmuir-Blodgett (LB) deposition, or the like. When the HTL is formed using vacuum deposition or spin coating, the conditions for deposition and coating may be similar to those for the formation of the HIL, though the conditions for the deposition and coating may vary according to the material that is used to form the HTL.

The HTL may be formed of any known hole-transporting materials. Non-limiting examples of suitable known HTL forming materials are carbazole derivatives, such as N-phenylcarbazole or polyvinylcarbazole, N,N'-bis(3-methylphenyl)-N,N'-diphenyl-[1,1-biphenyl]-4,4'-diamine (TPD), 4,4',4"-tris(N-carbazolyl)triphenylamine (TCTA), and N,N'-di(1-naphthyl)-N,N'-diphenylbenzidine) (NPB).

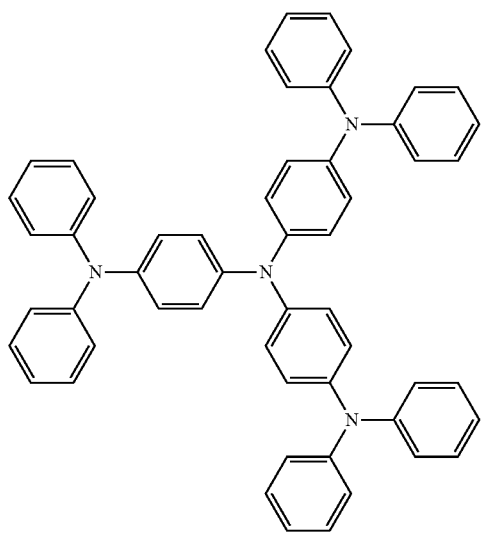

TDATA

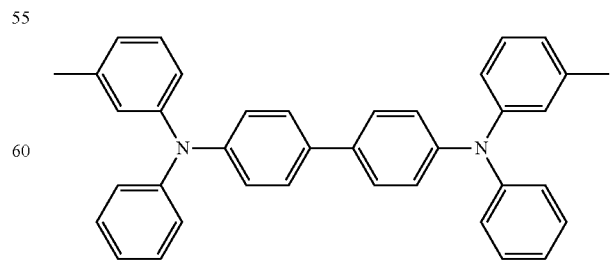

TPD

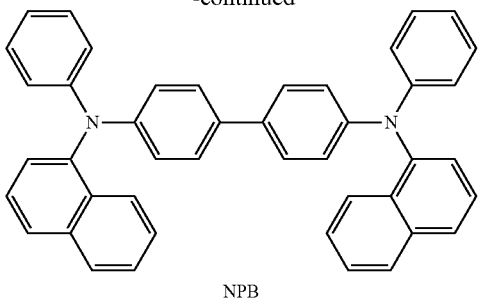

NPB

The thickness of the HTL may be from about 50 Å to about 2000 Å, and in some embodiments, from about 100 Å to about 1500 Å. When the thickness of the HTL is within these ranges, the HTL may have good hole transporting ability without a substantial increase in driving voltage.

The H-functional layer (having both hole injection and hole transport capabilities) may contain at least one material from each group of the hole injection layer materials and hole transport layer materials. The thickness of the H-functional layer may be from about 500 Å to about 10,000 Å, and in some embodiments, may be from about 100 Å to about 1,000 Å. When the thickness of the H-functional layer is within these ranges, the H-functional layer may have good hole injection and transport capabilities without a substantial increase in driving voltage.

In some embodiments, at least one of the HIL, HTL, and H-functional layer may include at least one of a compound of Formula 300 and a compound of Formula 350 below:

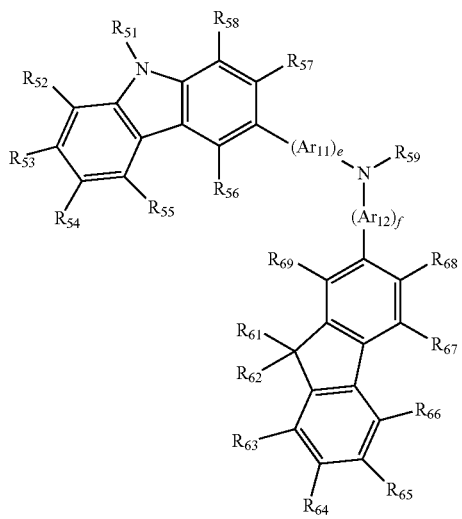

Formula 300

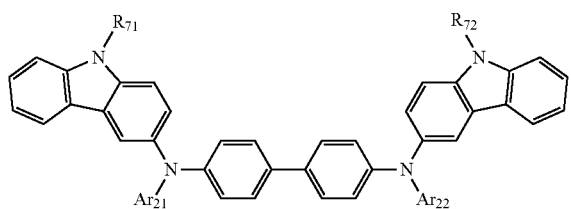

Formula 350

In Formulae 300 and 350, $Ar_{11}$, $Ar_{12}$, $Ar_{21}$, and $Ar_{22}$ may be each independently a substituted or unsubstituted $C_5$-$C_{60}$ arylene group.

In Formula 300, e and f may be each independently an integer from 0 to 5, for example, may be 0, 1, or 2. In a non-limiting embodiment, e may be 1, and f may be 0.

In Formulae 300 and 350 above, $R_{51}$ to $R_{58}$, $R_{61}$ to $R_{69}$, and $R_{71}$ and $R_{72}$ may be each independently hydrogen, deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_5$-$C_{60}$ aryl group, a substituted or unsubstituted $C_5$-$C_{60}$ aryloxy group, or a substituted or unsubstituted $C_5$-$C_{60}$ arylthio group.

The unsubstituted $C_1$-$C_{60}$ alkyl group used herein may be linear or branched. Examples of the alkyl group may include, but are not limited to, a methyl group, an ethyl group, a propyl group, an isobutyl group, a sec-butyl group, a pentyl group, an iso-amyl group, a hexyl group, a heptyl group, an octyl group, a nonanyl group, and a dodecyl group. At least one hydrogen atom of the alkyl group may be substituted with deuterium, a halogen atom, a hydroxyl group, a nitro group, a cyano group, an amino group, an amidino group, hydrazine, hydrazone, a carboxyl group or a salt thereof, a sulfonic acid group or a salt thereof, a phosphoric acid group or a salt thereof, a $C_1$-$C_{10}$ alkyl group, a $C_1$-$C_{10}$ alkoxy group, a $C_2$-$C_{10}$ alkenyl group, a $C_2$-$C_{10}$ alkynyl group, a $C_6$-$C_{16}$ aryl group, or a $C_4$-$C_{16}$ heteroaryl group.

The unsubstituted $C_2$-$C_{60}$ alkenyl group may indicate an unsaturated alkyl groups having at least one carbon-carbon double bond in the center or at a terminal of the alkyl group. Examples of the alkenyl group may be an ethenyl group, a propenyl group, a butenyl group, and the like. At least one hydrogen atom in the unsubstituted alkenyl group may be substituted with a substituent described above in conjunction with the alkyl group.

The unsubstituted $C_2$-$C_{60}$ alkynyl group may indicate an alkyl group having at least one carbon-carbon triple bond in the center or at a terminal of the alkyl group. Non-limiting examples of the unsubstituted $C_2$-$C_{20}$ alkynyl group may be acetylene, propylene, phenylacetylene, naphthylacetylene, isopropylacetylene, t-butylacetylene, and diphenylacetylene. At least one hydrogen atom in the alkynyl group may be substituted with a substituent described above in conjunction with the alkyl group.

The unsubstituted $C_3$-$C_{60}$ cycloalkyl group may indicate a $C_3$-$C_{60}$ cyclic alkyl group wherein at least one hydrogen atom in the cycloalkyl group may be substituted with a substituent described above in conduction with the $C_1$-$C_{60}$ alkyl group.

The unsubstituted $C_1$-$C_{60}$ alkoxy group may indicate a group having a structure of —OA wherein A is an unsubstituted $C_1$-$C_{60}$ alkyl group as described above. Non-limiting examples of the unsubstituted $C_1$-$C_{60}$ alkoxy group may be a methoxy group, an ethoxy group, a propoxy group, an isopropyloxy group, a butoxy group, and a pentoxy group. At least one hydrogen atom of the alkoxy group may be substituted with a substituent such as those described above in conjunction with the alkyl group.

The unsubstituted $C_5$-$C_{60}$ aryloxy group may be a group represented by —$OA_1$ wherein $A_1$ may be a $C_6$-$C_{60}$ aryl group. An example of the aryloxy group may be a phenoxy group. At least one hydrogen atom in the aryloxy group may be substituted with a substituent described above in conjunction with the unsubstituted $C_1$-$C_{60}$ alkyl group.

The unsubstituted $C_5$-$C_{60}$ arylthio group may be a group represented by —$SA_1$ where $A_1$ may be a $C_6$-$C_{60}$ aryl group. Non-limiting examples of the arylthio group may be a benzenethio group and a naphthylthio group. At least one hydrogen atom in the arylthio group may be substituted with a substituent described above in conjunction with the unsubstituted $C_1$-$C_{60}$ alkyl group.

The unsubstituted $C_5$-$C_{60}$ arylene group used herein may refer to a divalent group having a carbocyclic aromatic system having 5 to 60 carbon atoms, and the divalent group may be a monocyclic or polycyclic group. Examples of the unsubstituted $C_5$-$C_{60}$ arylene group may be understood by referring to the examples of the unsubstituted $C_5$-$C_{60}$ aryl group. At least one hydrogen atom in the arylene group may be substituted with a substituent described above in conjunction with the unsubstituted $C_1$-$C_{60}$ alkyl group.

In some embodiments, in Formulae 300 and 350 above, $R_{51}$ to $R_{58}$, $R_{61}$ to $R_{69}$, $R_{71}$ and $R_{72}$ may be each independently one of hydrogen; deuterium; a halogen atom; a hydroxyl group; a cyano group; a nitro group; an amino group; an amidino group; hydrazine; hydrazone; a carboxyl group or a salt thereof; a sulfonic acid group or a salt thereof; a phosphoric acid group or a salt thereof; a $C_1$-$C_{10}$ alkyl group (for example, a methyl group, an ethyl group, a propyl group, a butyl group, a pentyl group, a hexyl group, or the like); a $C_1$-$C_{10}$ alkoxy group (for example, a methoxy group, an ethoxy group, a propoxy group, a butoxy group, a pentoxy group, or the like); a $C_1$-$C_{10}$ alkyl group and a $C_1$-$C_{10}$ alkoxy group that are substituted with at least one of deuterium, a halogen atom, a hydroxyl group, a cyano group, a nitro group, an amino group, an amidino group, hydrazine, hydrazone, a carboxyl group or a salt thereof, a sulfonic acid group or a salt thereof, and a phosphoric acid group or a salt thereof; a phenyl group; a naphthyl group; an anthryl group; a fluorenyl group; a pyrenyl group; and a phenyl group, a naphthyl group, an anthryl group, a fluorenyl group, and a pyrenyl group that are substituted with at least one of deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid group or a salt thereof, a $C_1$-$C_{10}$ alkyl group, and a $C_1$-$C_{10}$ alkoxy group.

In Formula 300, $R_{59}$ may be one of a phenyl group, a naphthyl group, an anthryl group, a biphenyl group, a pyridyl group; and a phenyl group, a naphthyl group, an anthryl group, a biphenyl group, and a pyridyl group that are substituted with at least one of deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid group or a salt thereof, a substituted or unsubstituted $C_1$-$C_{20}$ alkyl group, and a substituted or unsubstituted $C_1$-$C_{20}$ alkoxy group.

In an embodiment of the present invention, the compound of Formula 300 may be a compound represented by Formula 300A below:

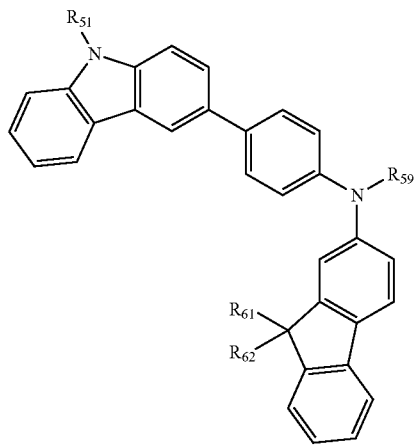

Formula 300A

In Formula 300A, $R_{51}$, $R_{61}$, $R_{62}$, and $R_{59}$ may be as defined above.

In some non-limiting embodiments, at least one of the HIL, HTL, and H-functional layer may include at least one of compounds represented by Formulae 301 to 320 below:

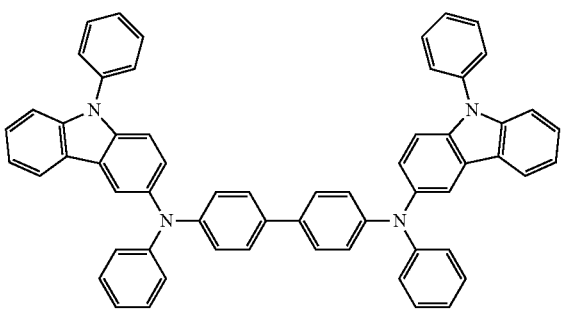

301

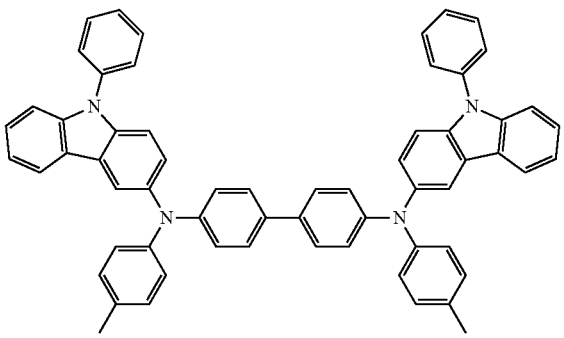

302

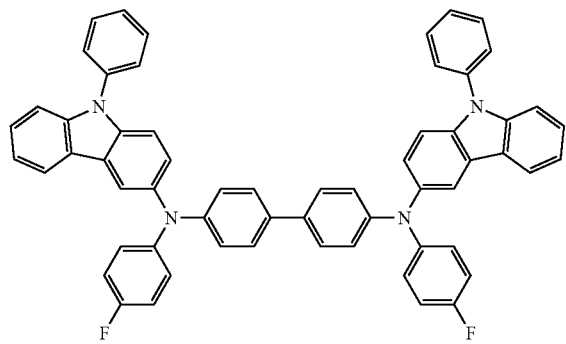
303
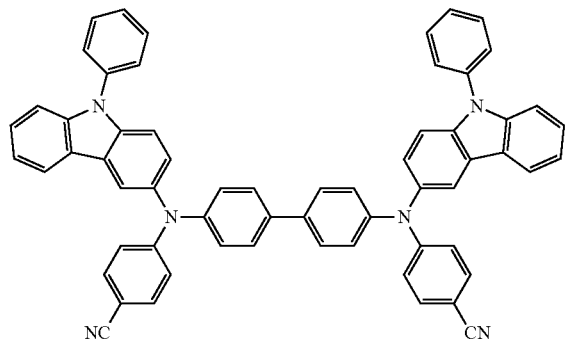
304
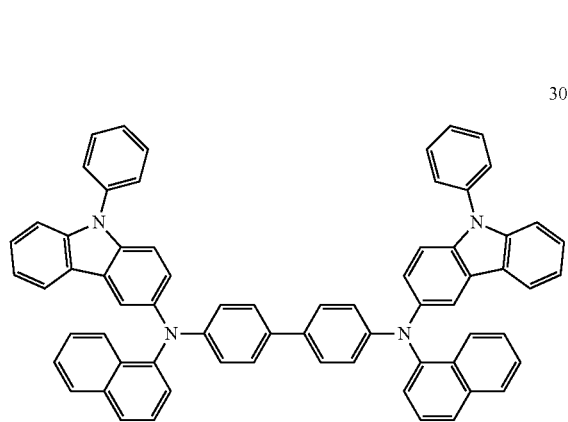
305
306
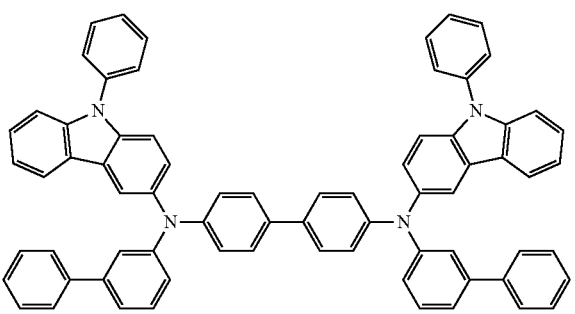
307
308
309

310
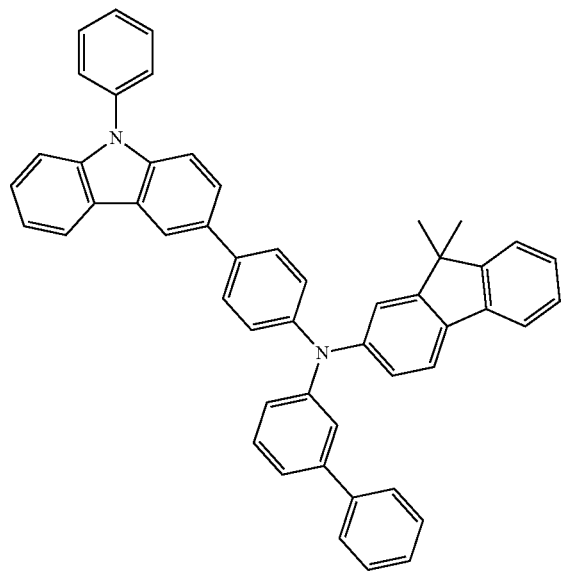
311
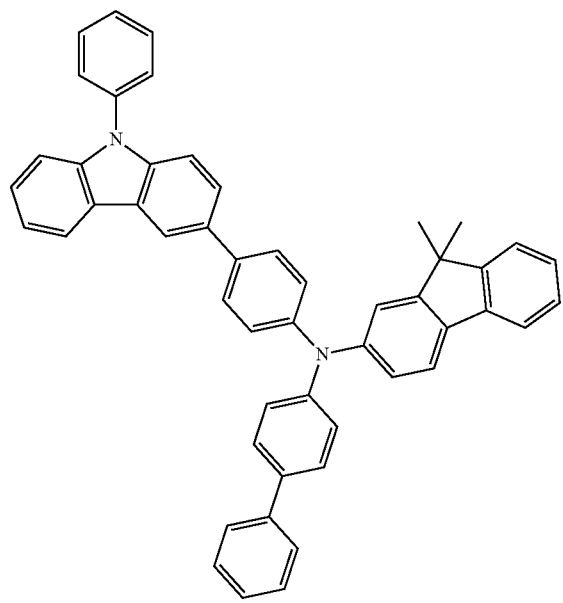
312
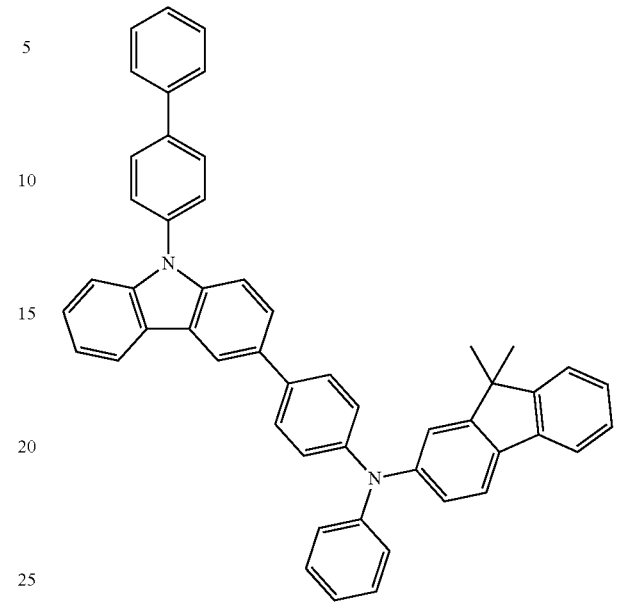
313
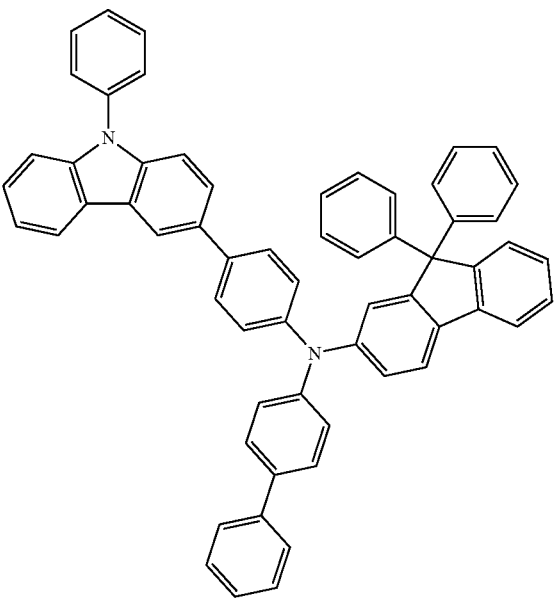

314
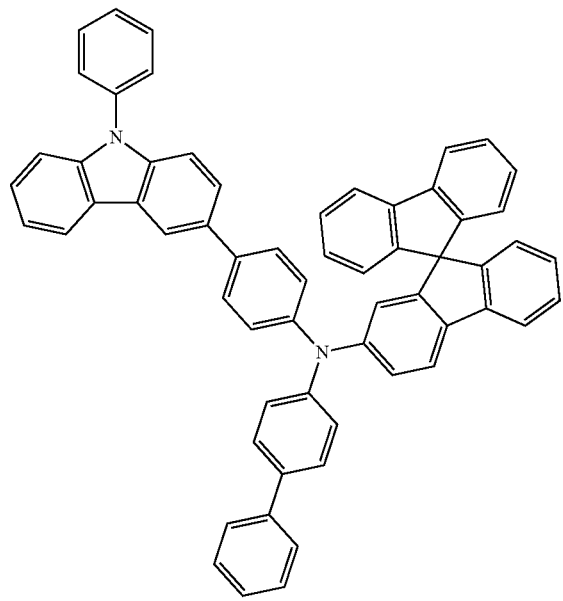
315
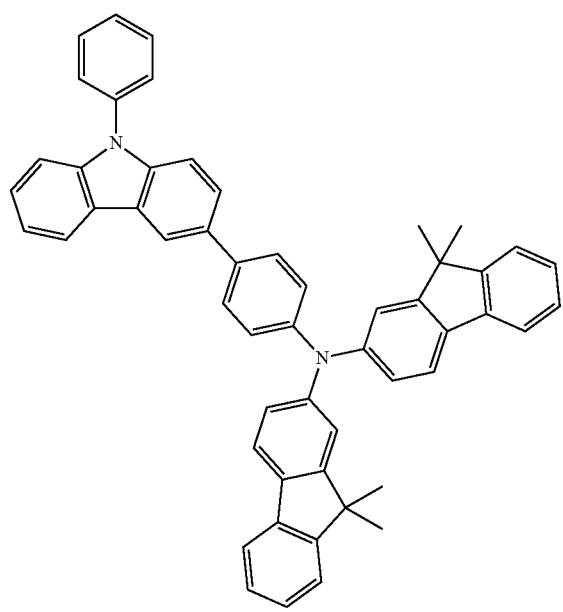
316
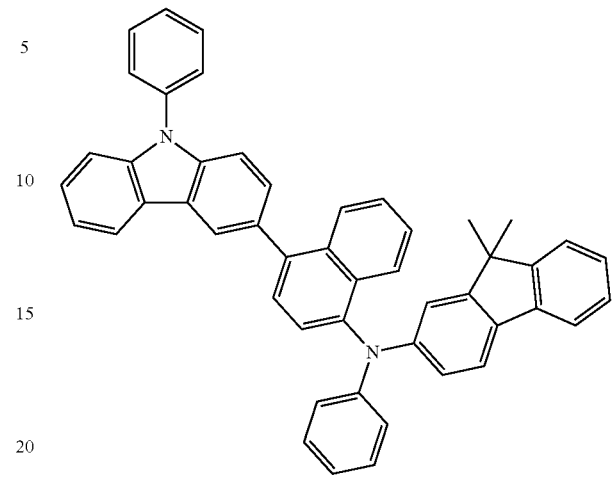
317
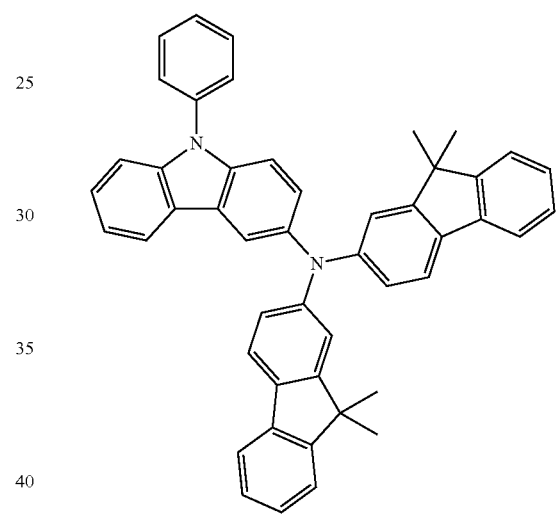
318
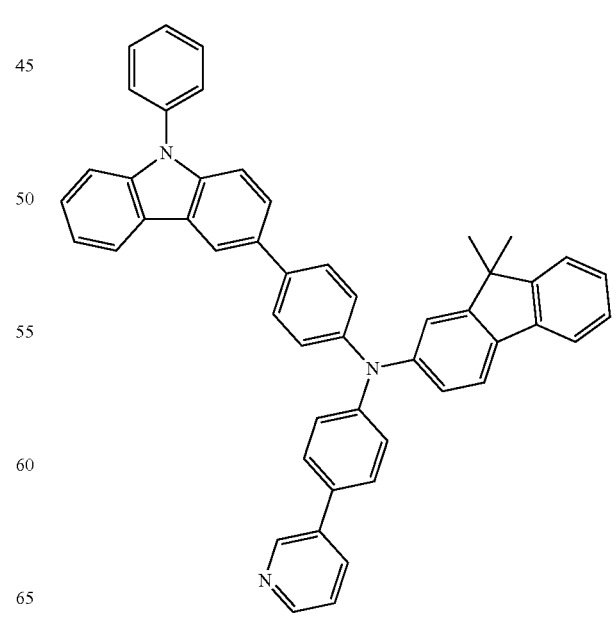

-continued

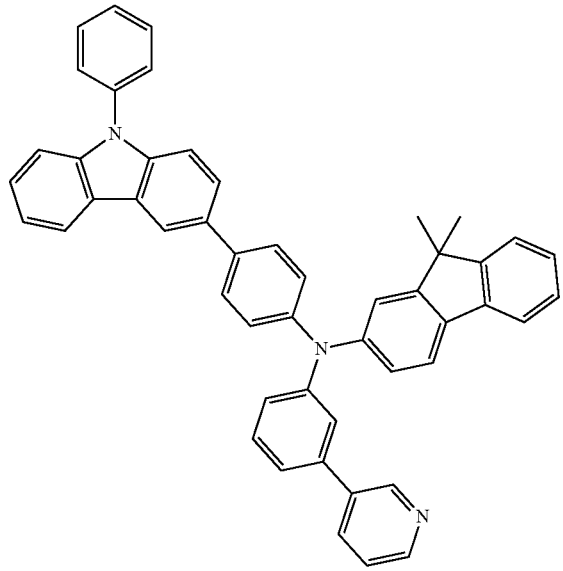
319

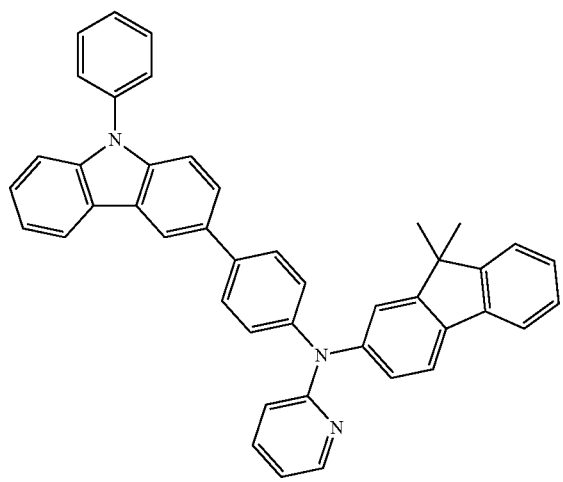
320

At least one of the HIL, HTL, and H-functional layer may further include a charge-generating material for improved layer conductivity, in addition to a known hole injecting material, hole transport material, and/or material having both hole injection and hole transport capabilities as described above.

The charge-generating material may be, for example, a p-type dopant. The p-type dopant may be one of quinine derivatives, metal oxides, and compounds with a cyano group, but are not limited thereto. Non-limiting examples of the p-type dopant may be quinone derivatives such as tetracyanoquinonedimethane (TCNQ), 2,3,5,6-tetrafluoro-tetracyano-1,4-benzoquinonedimethane (F4-CTNQ), and the like; metal oxides such as tungsten oxide, molybdenum oxide, and the like; and cyano-containing compounds such as Compound 200 below.

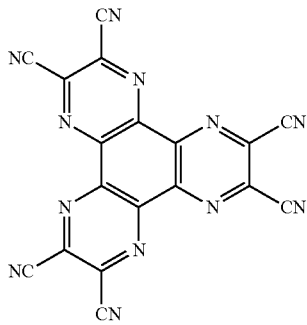
Compound 200

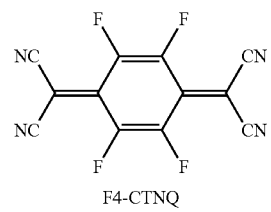
F4-CTNQ

When the hole injection layer, the hole transport layer, or the H-functional layer further includes a charge-generating material, the charge-generating material may be homogeneously dispersed or inhomogeneously distributed in the layer.

A buffer layer may be disposed between at least one of the HIL, HTL, and H-functional layer, and the EML. The buffer layer may compensate for an optical resonance distance of light according to a wavelength of the light emitted from the EML, and thus may increase efficiency. The butter layer may include any hole injecting material or hole transporting material that are widely known. In embodiments, the buffer layer may include the same material as one of the materials included in the HIL, HTL, and H-functional layer that underlie the buffer layer.

Then, an EML may be formed on the HTL, H-functional layer, or buffer layer by vacuum deposition, spin coating, casting, Langmuir-Blodget (LB) deposition, or the like. When the EML is formed using vacuum deposition or spin coating, the deposition and coating conditions may be similar to those for the formation of the HIL, though the conditions for deposition and coating may vary according to the material that is used to form the EML.

The EML may be formed using the organic compound of Formula 1 above, or any of a variety of known light-emitting materials, such as known hosts and dopants. Any of known fluorescent and phosphorescent dopants may be used.

Non-limiting example of the host may be Alq$_3$, 4,4'-N,N'-dicarbazole-biphenyl (CBP), poly(n-vinylcarbazole) (PVK), 9,10-di(naphthalene-2-yl)anthracene (ADN), 4,4',4"-Tris (carbazol-9-yl)-triphenylamine (TCTA), 1,3,5-tris(N-phenylbenzimidazole-2-yl)benzene (TPBI), 3-tert-butyl-9,10-di-2-naphthylanthracene (TBADN), E3, distyrylarylene (DSA), dmCBP (see a formula below), and Compounds 501 to 509 below.

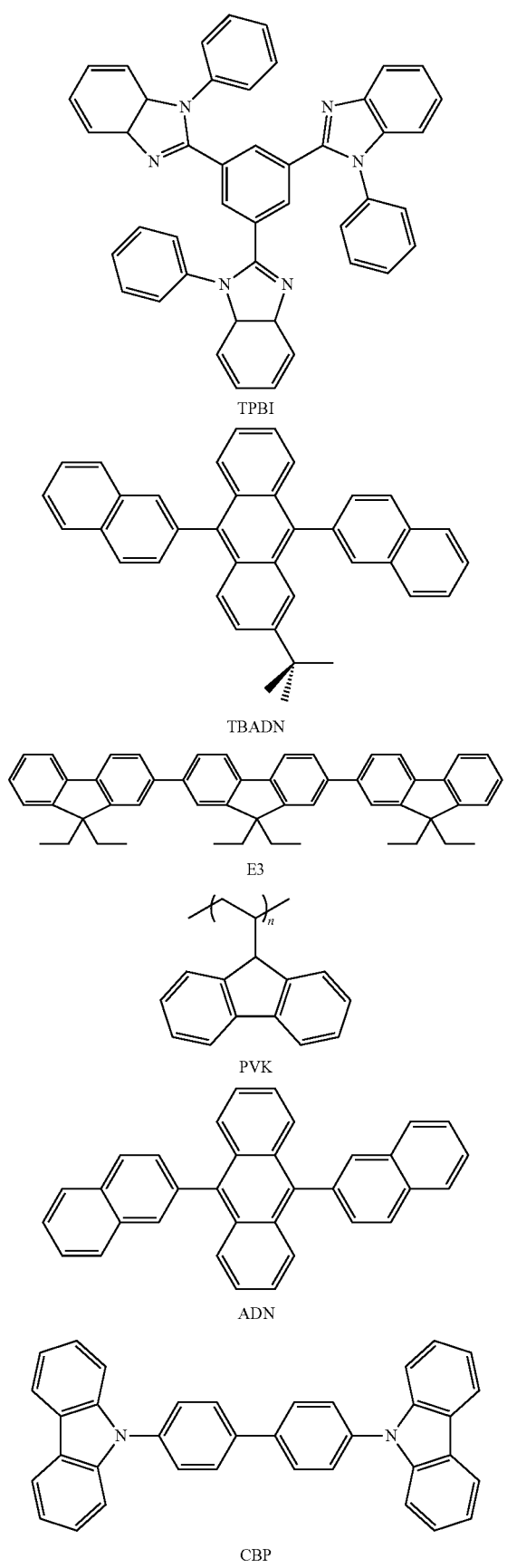
TPBI
TBADN
E3
PVK
ADN
CBP
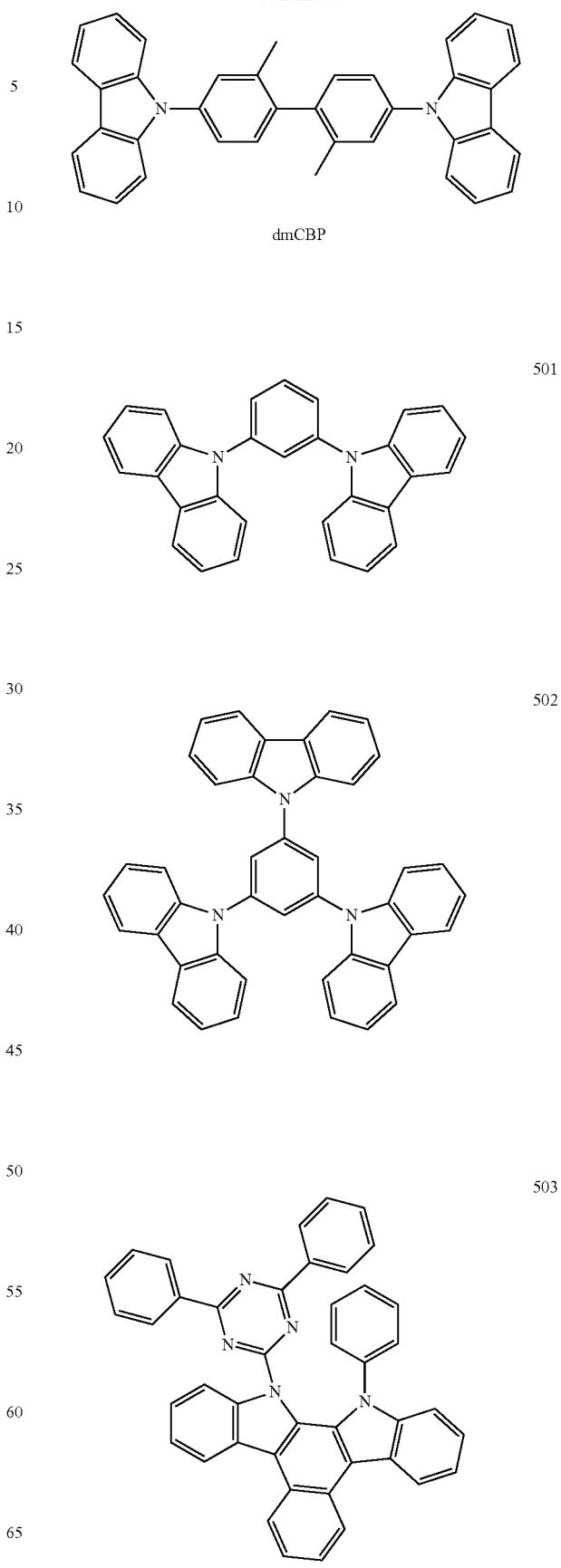
dmCBP
501
502
503

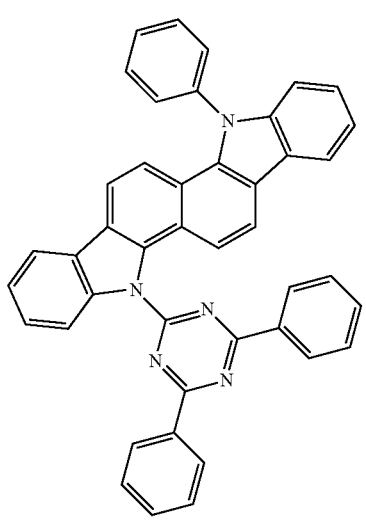
504

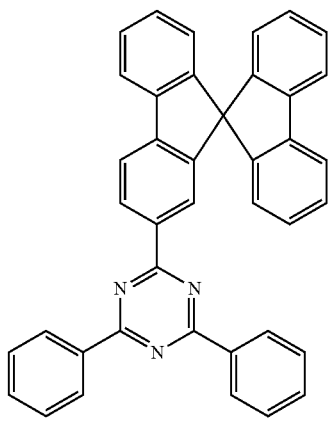
507

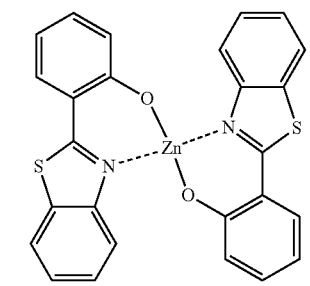
508

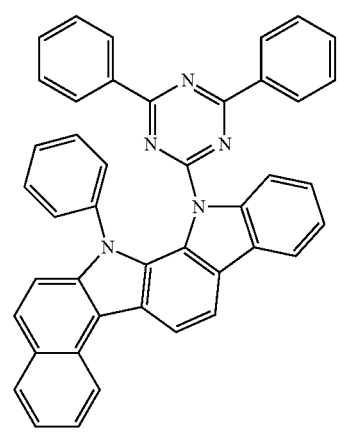
505

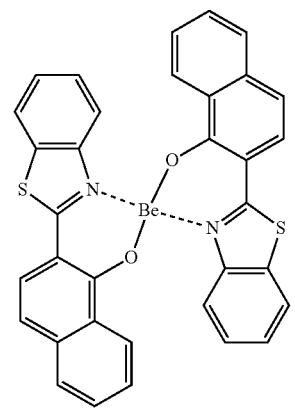
509

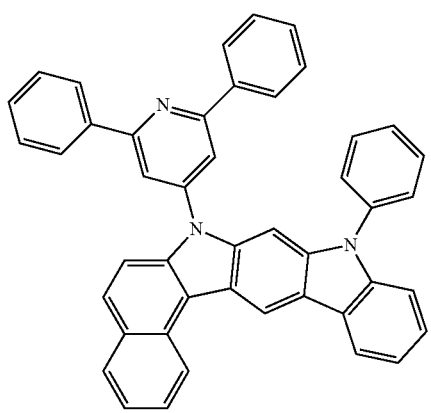
506

In some embodiments, an anthracene-based compound represented by Formula 400 below may be used as the host.

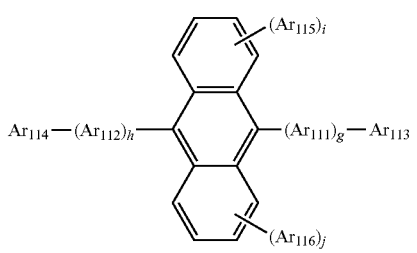

Formula 400

In Formula 400, $Ar_{111}$ and $Ar_{112}$ may be each independently a substituted or unsubstituted $C_5$-$C_{60}$ arylene group; $Ar_{113}$ to $Ar_{116}$ may be each independently a substituted or unsubstituted $C_1$-$C_{10}$ alkyl group, or a substituted or unsubstituted $C_5$-$C_{60}$ aryl group; and g, h, i, and j may be each independently an integer from 0 to 4.

In some non-limiting embodiments, $Ar_{111}$ and $Ar_{112}$ in Formula 400 may be each independently a phenylene group, a naphthylene group, a phenanthrenylene group, or a pyrenylene group; or a phenylene group, a naphthylene group, a phenanthrenylene group, a fluorenyl group, or a pyrenylene group that are substituted with at least one of a phenyl group, a naphthyl group, and an anthryl group.

In Formula 400 above, g, h, i, and j may be each independently 0, 1, or 2.

In Formula 400, $Ar_{113}$ to $Ar_{116}$ may be each independently one of a $C_1$-$C_{10}$ alkyl group substituted with at least one of a phenyl group, a naphthyl group, and an anthryl group; a phenyl group; a naphthyl group; an anthryl group; a pyrenyl group; a phenanthrenyl group; a fluorenyl group; a phenyl group, a naphthyl group, an anthryl group, a pyrenyl group, a phenanthrenyl group, and a fluorenyl group that are substituted with at least one of deuterium, a halogen atom, a hydroxyl group, a cyano group, a nitro group, an amino group, an amidino groups, hydrazine, hydrazone, a carboxylic group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthryl group, a pyrenyl group, a phenanthrenyl group, and a fluorenyl group; and

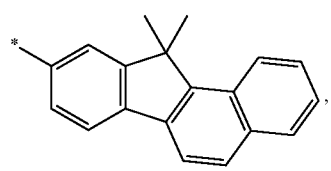 [SMILES: *c1ccc2c(c1)C(C)(C)c1c-2ccc2ccccc12 ; ","]

but are not limited thereto.

For example, the anthracene compound of Formula 400 above may be one of the compounds represented by the following formulae, but is not limited thereto:

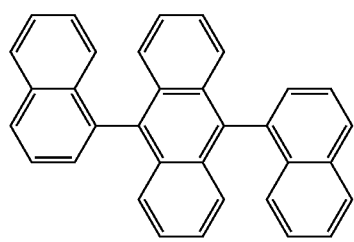

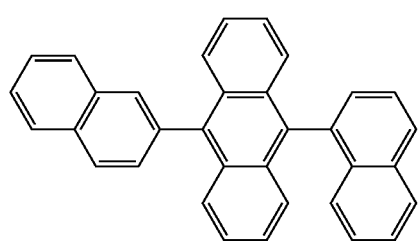

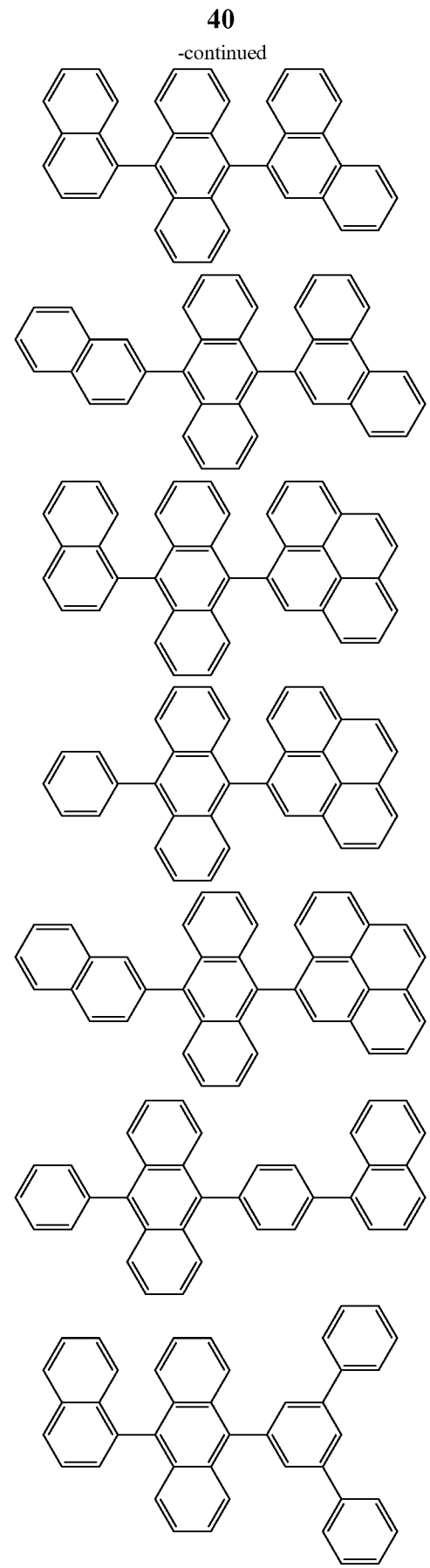

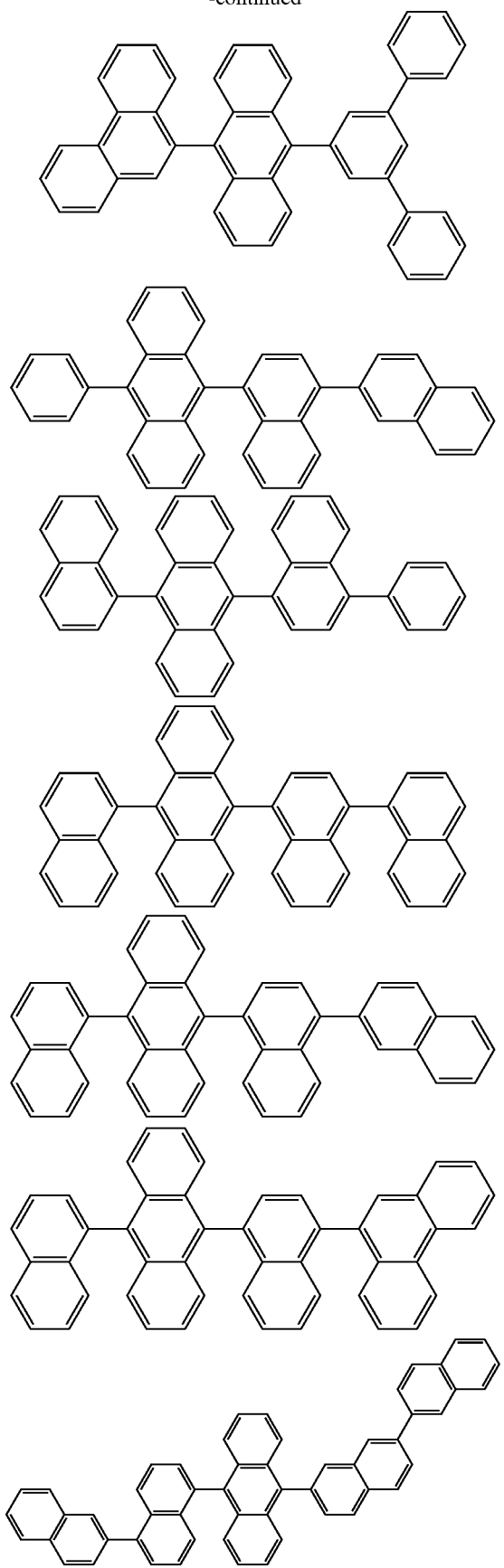
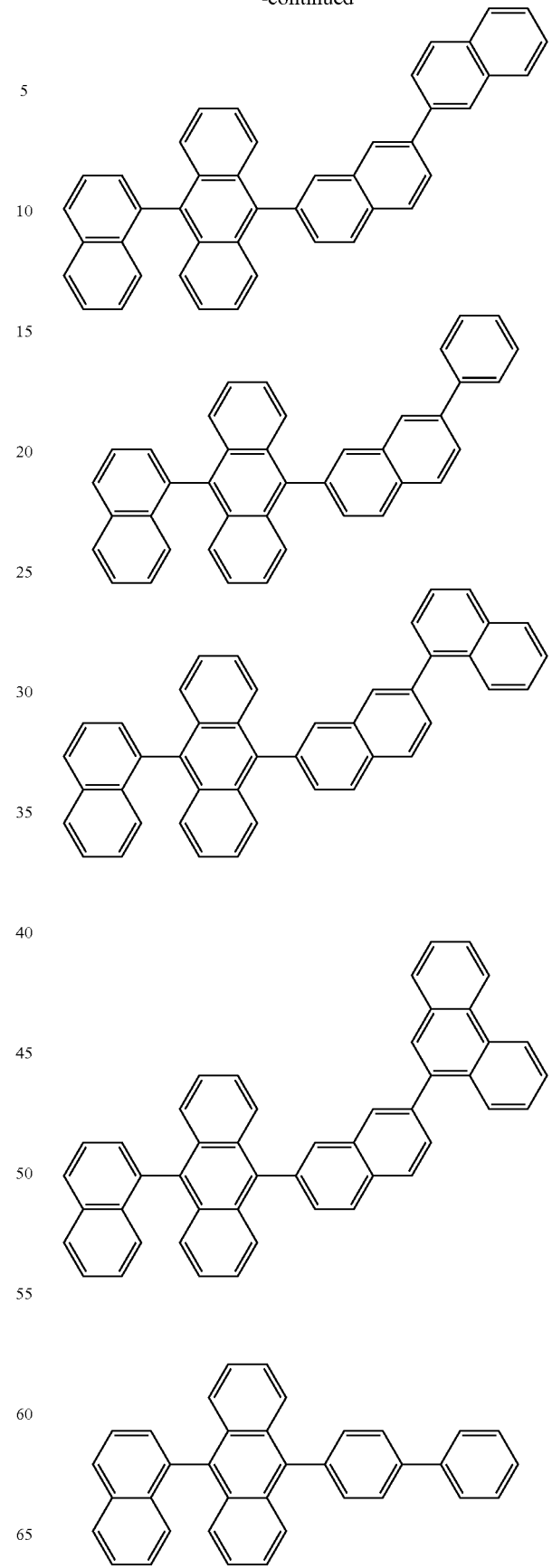

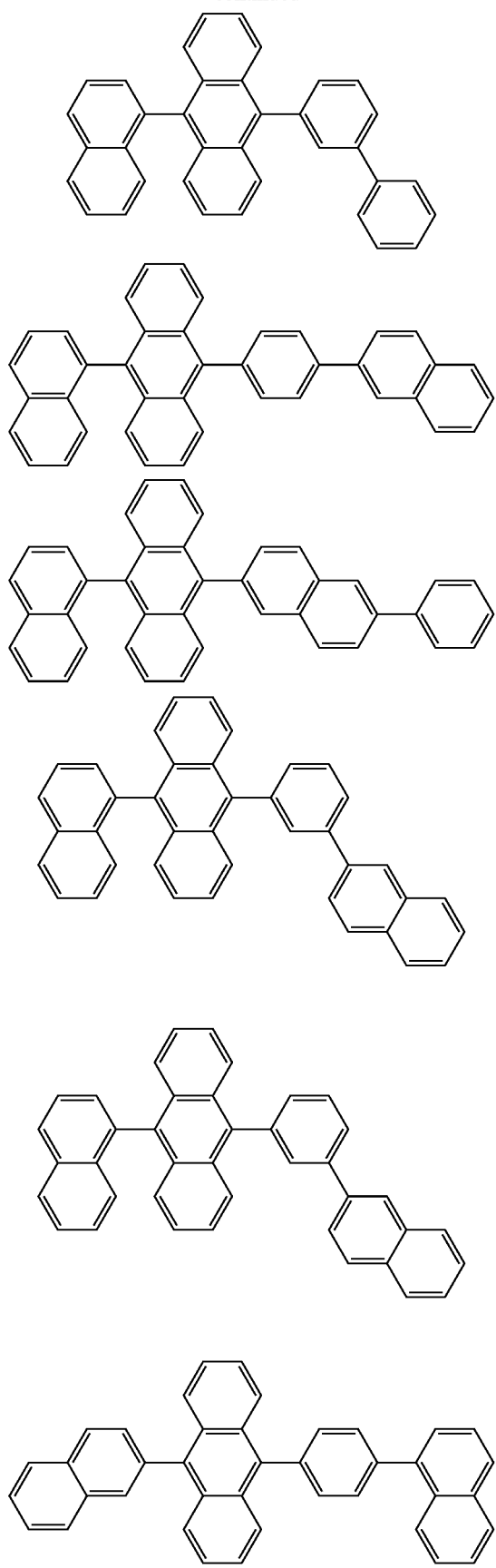

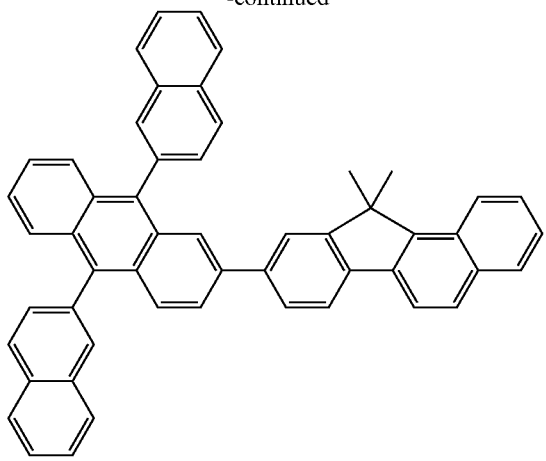
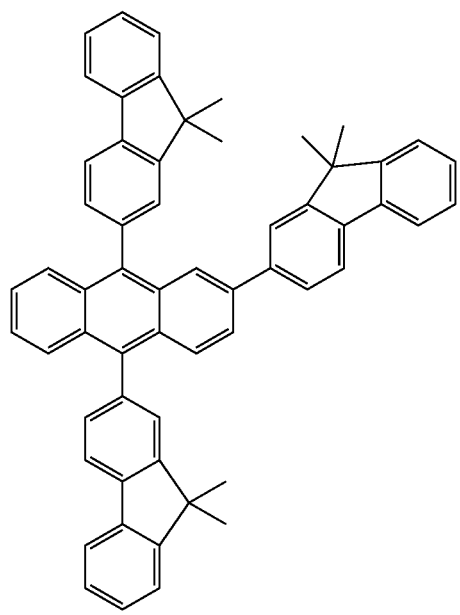
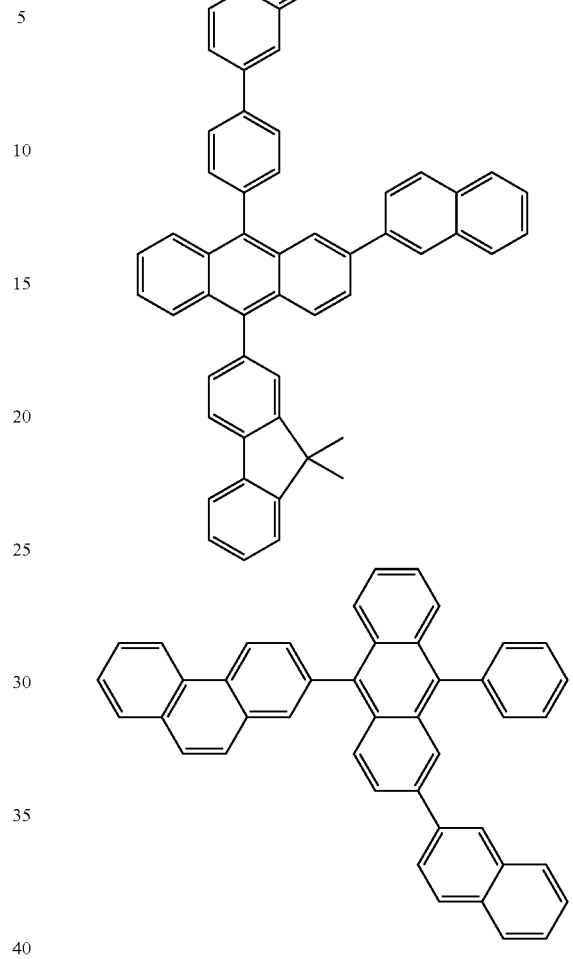

In some embodiments, an anthracene-based compound represented by Formula 401 below may be used as the host.

Formula 401

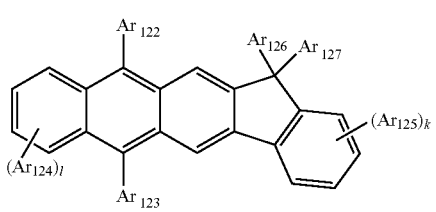

In Formula 401, $Ar_{122}$ to $Ar_{125}$ may be as defined above in connection with $Ar_{113}$ in Formula 400.

In Formula 401, $Ar_{126}$ and $Ar_{127}$ may be each independently a $C_1$-$C_{10}$ alkyl group (for example, a methyl group, an ethyl group, or a propyl group).

In Formula 401, k and l may be each independently an integer from 0 to 4, for example, 0, 1, or 2.

For example, the anthracene compound of Formula 401 above may be one of the compounds represented by the following formulae, but is not limited thereto:

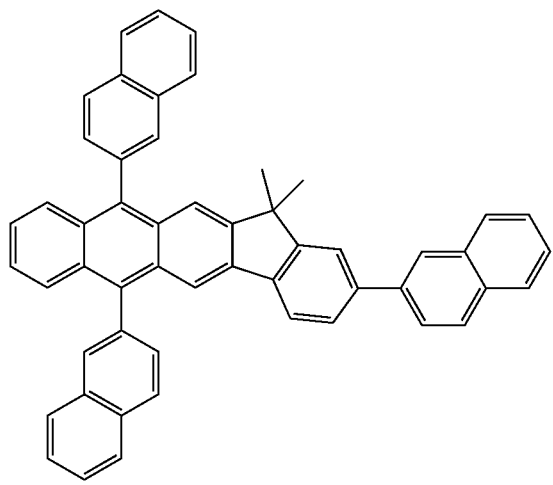

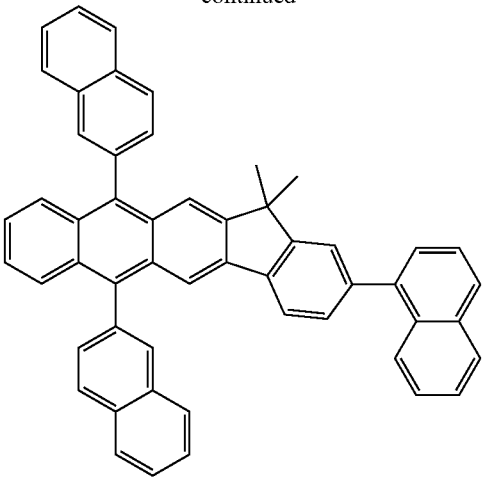

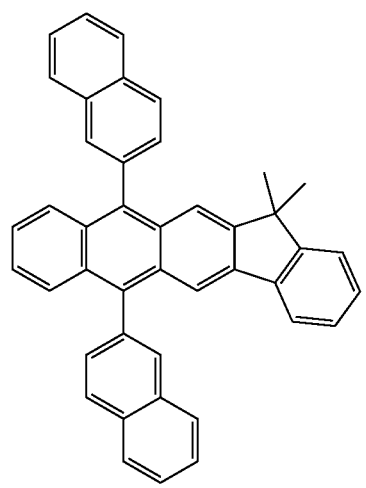

When the organic light-emitting device is a full color organic light-emitting device, the emission layer may be patterned into a red emission layer, a green emission layer, and a blue emission layer.

At least one of the red EML, the green EML, and the blue EML may include a dopant below (ppy=phenylpyridine).

Non-limiting examples of the blue dopant may be compounds represented by the following formulae.

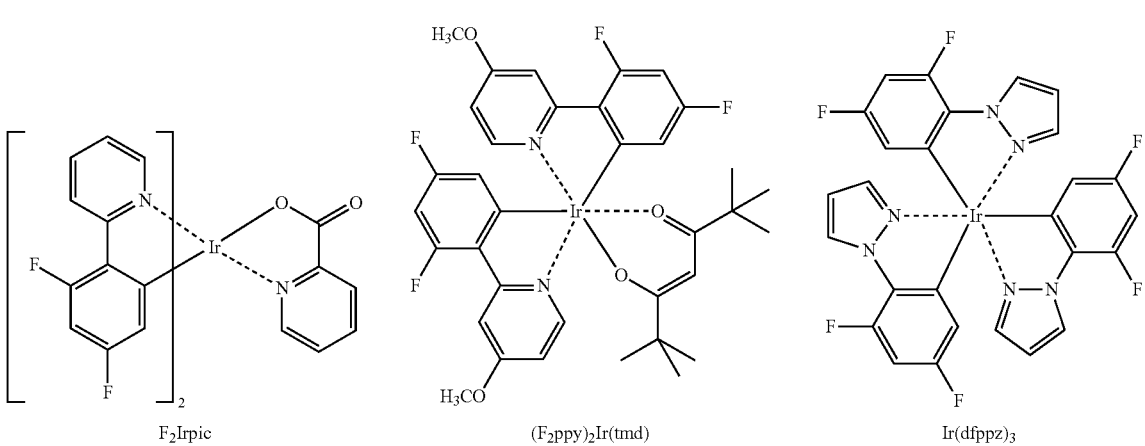

-continued
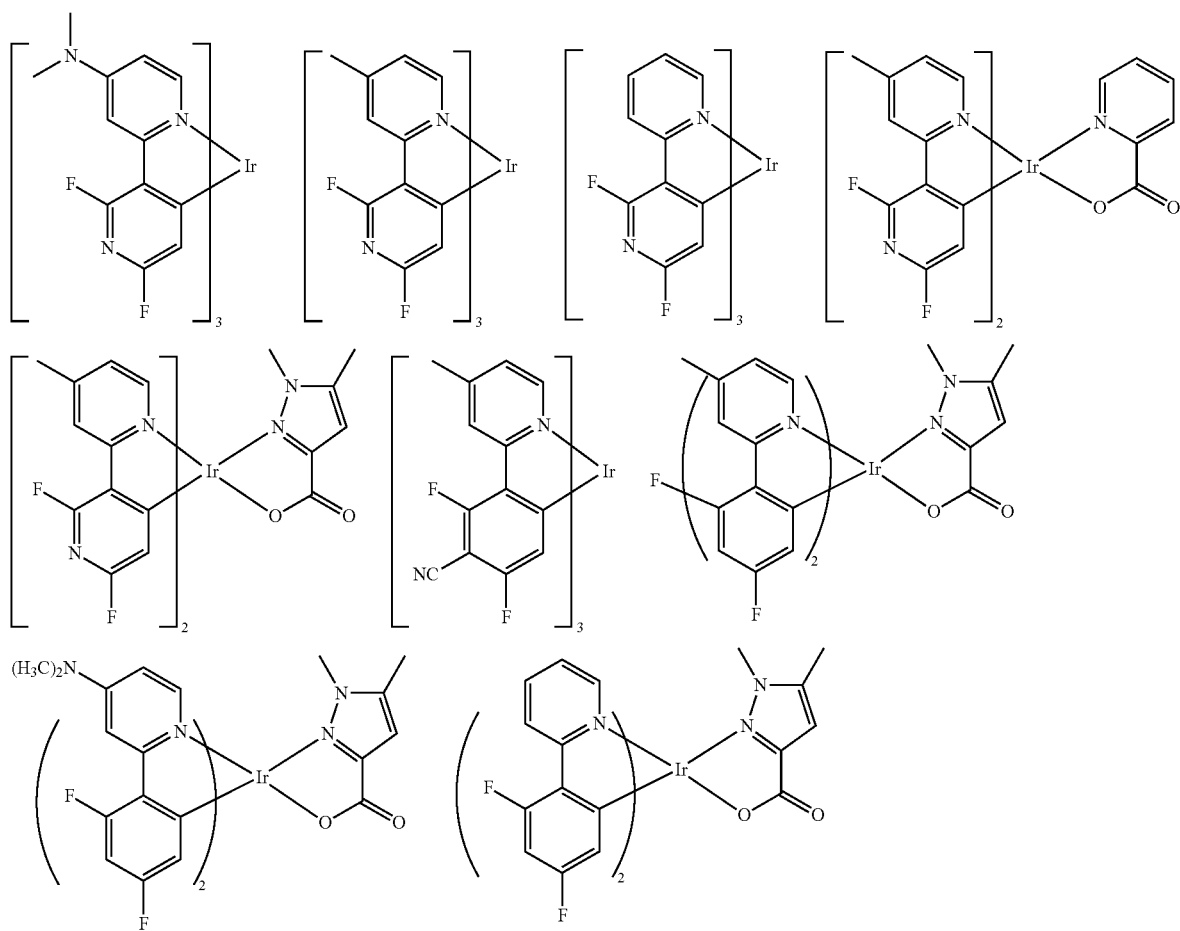
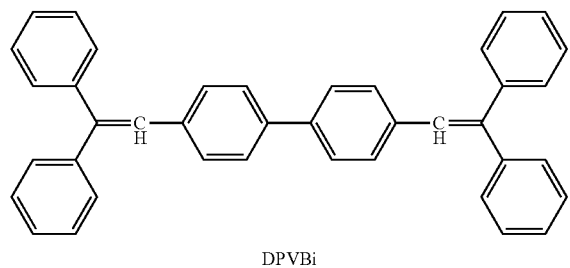
DPVBi
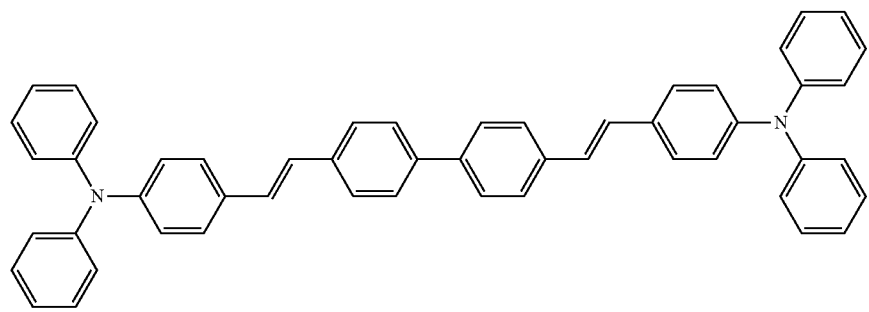
DPAVBi

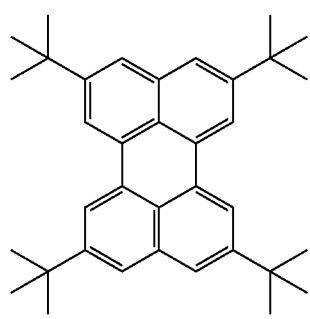
TBPe
Non-limiting examples of the red dopant may be compounds represented by the following formulae.
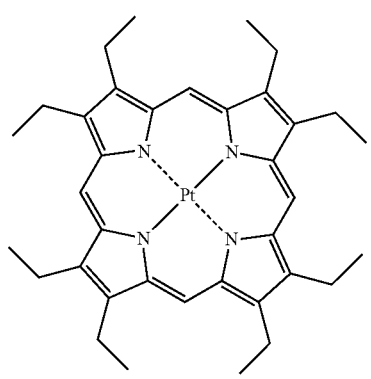
PtOEP
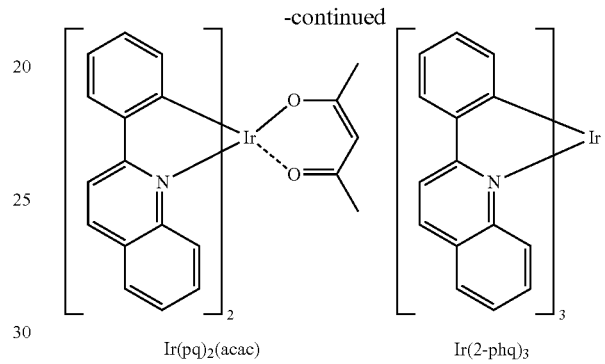
Ir(pq)₂(acac)   Ir(2-phq)₃
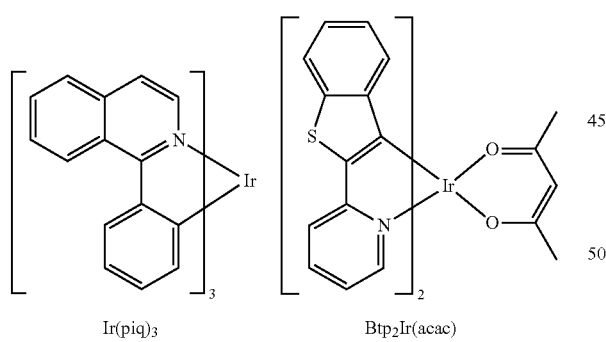
Ir(piq)₃   Btp₂Ir(acac)
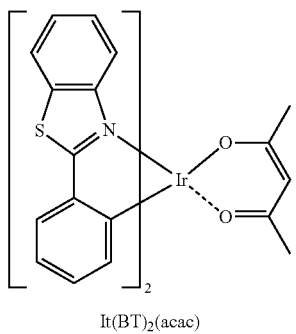
It(BT)₂(acac)
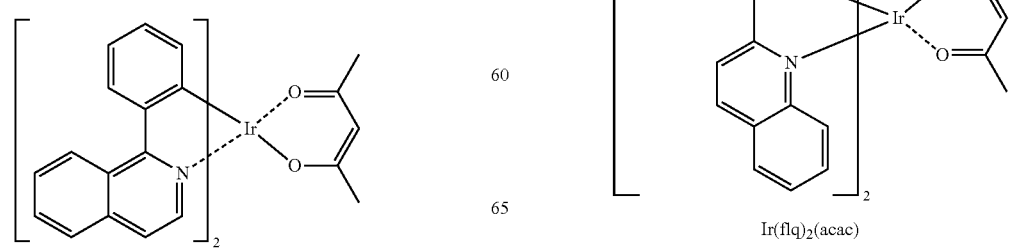
Ir(flq)₂(acac)

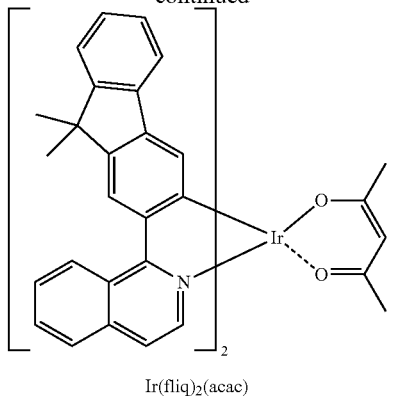
Ir(fliq)₂(acac)
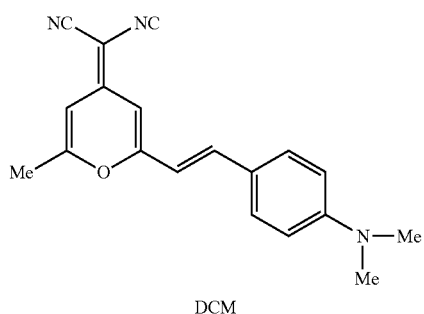
DCM
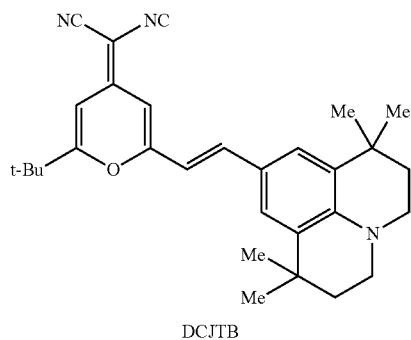
DCJTB
Non-limiting examples of the green dopant may be compounds represented by the following formulae.
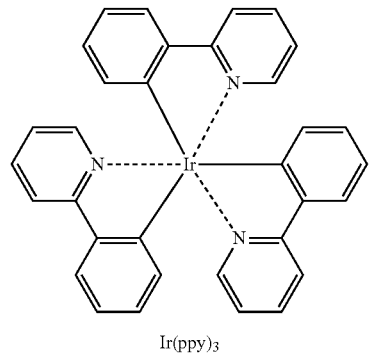
Ir(ppy)₃
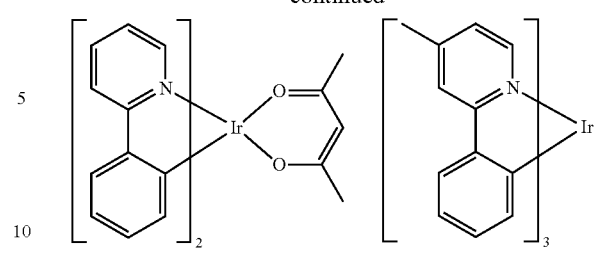
Ir(ppy)₂(acac)   Ir(mpyp)₃
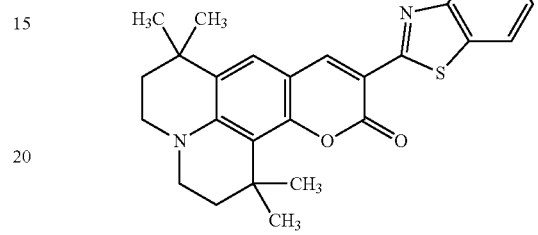
C545T
Non-limiting examples of the dopant that may be used in the EML may be Pt complexes represented by the following formulae.
D1
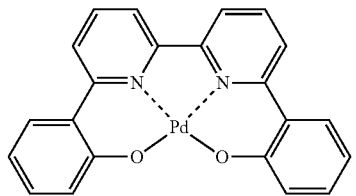
D2
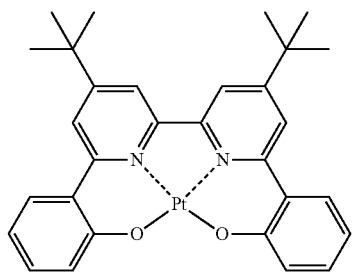
D3
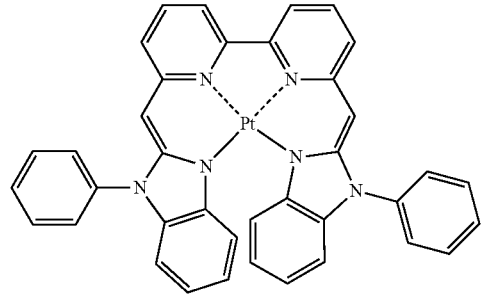

D4 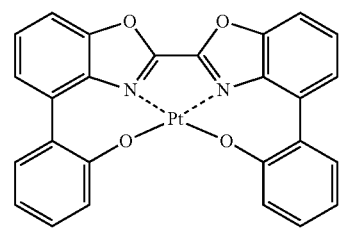
D5 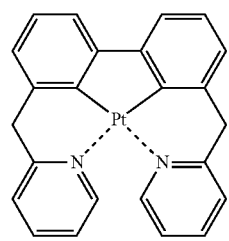
D6 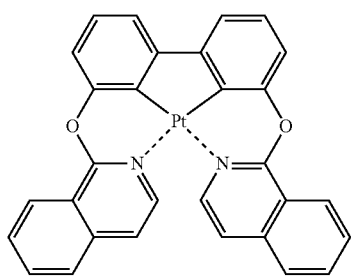
D7 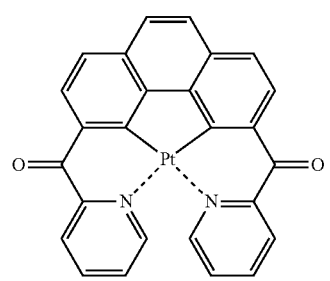
D8 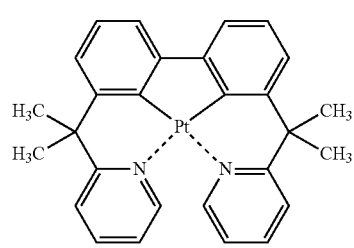
D9 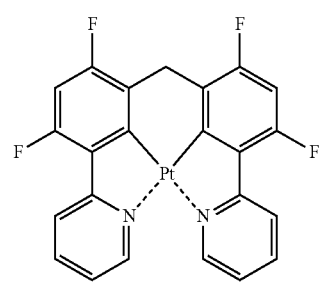
D10 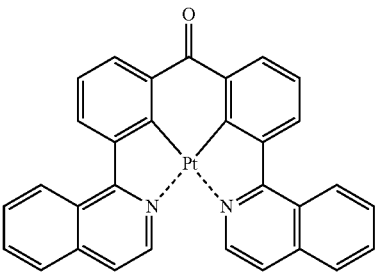
D11 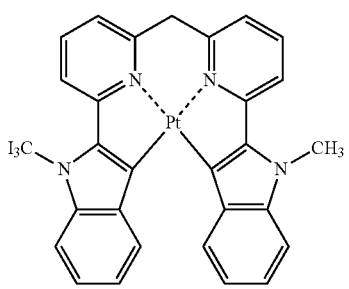
D12 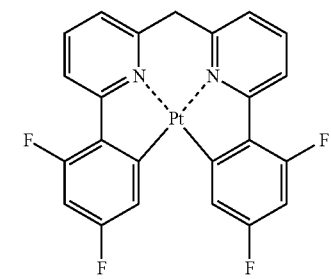
D13 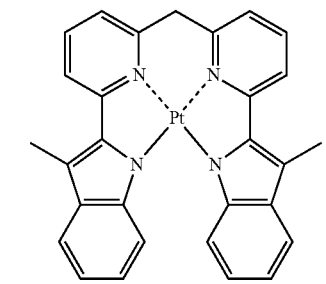
D14 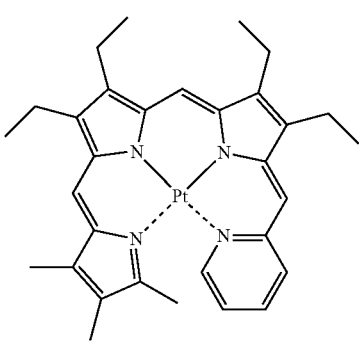

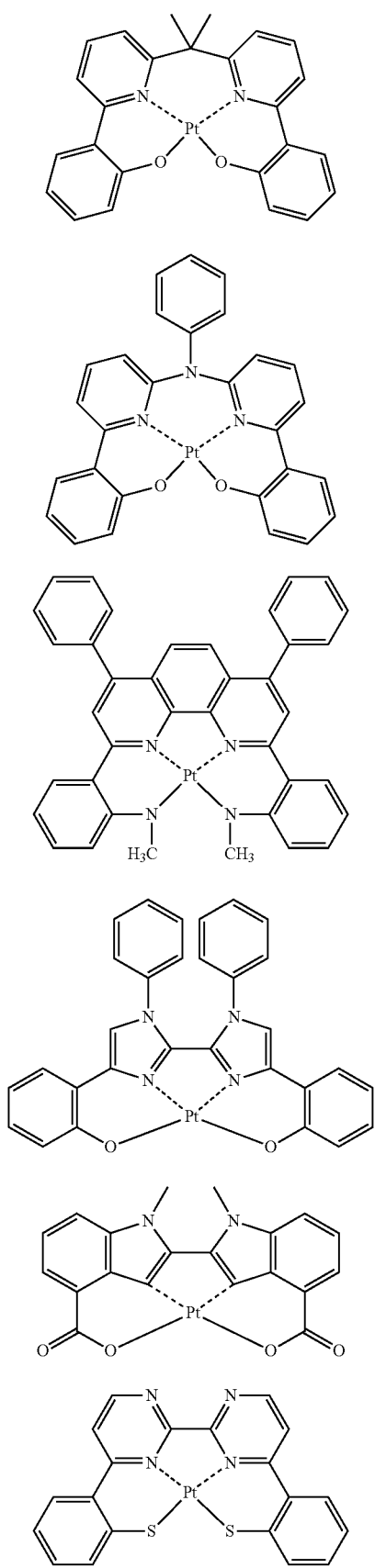
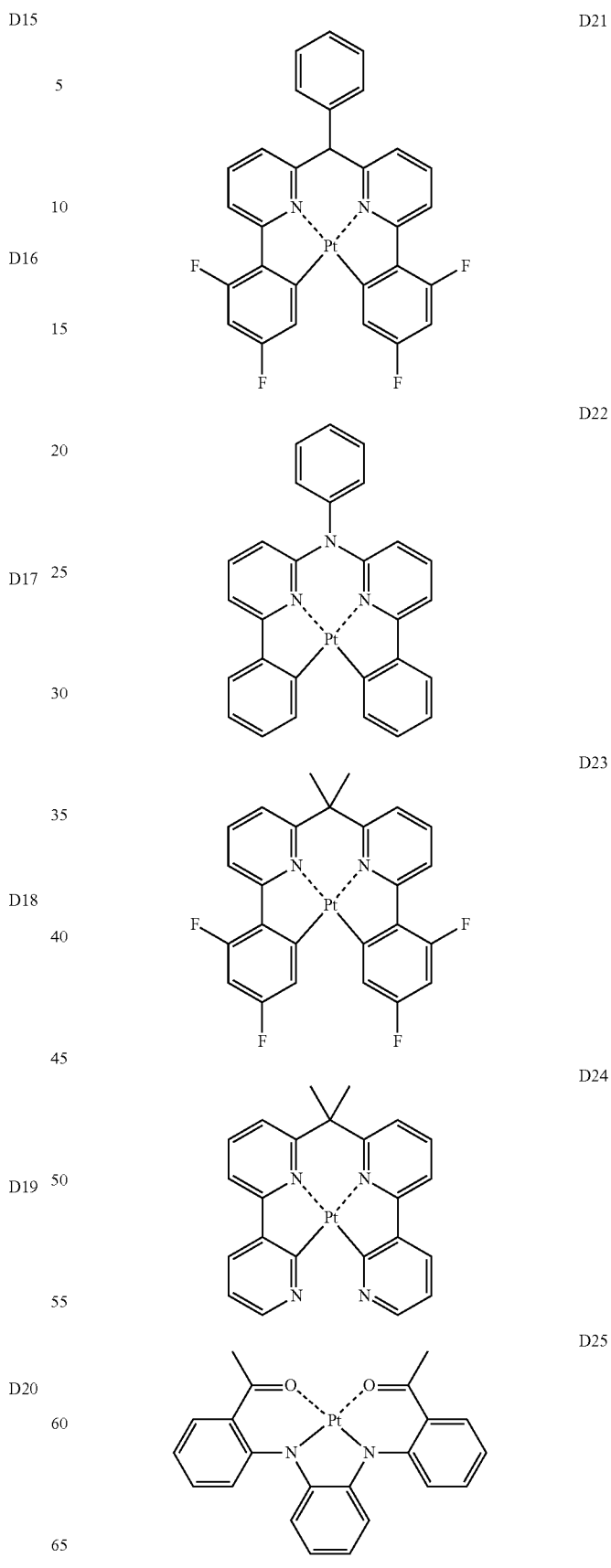

-continued
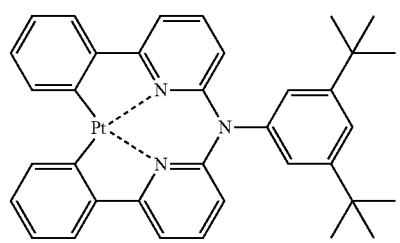
D26
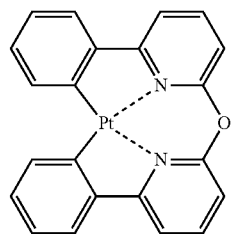
D27
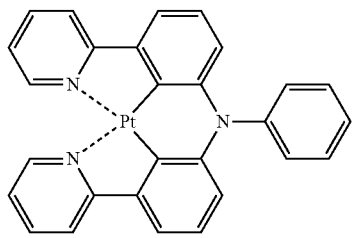
D28
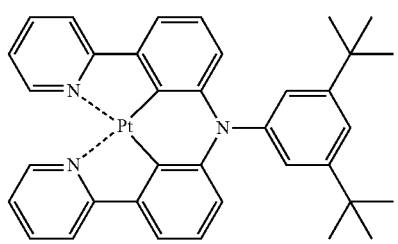
D29
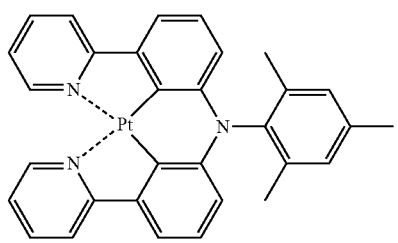
D30
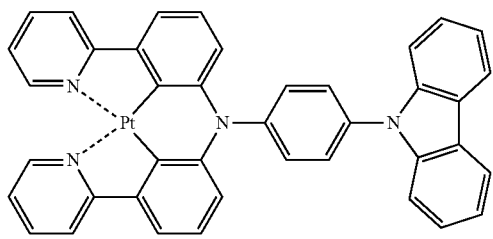
D31
-continued
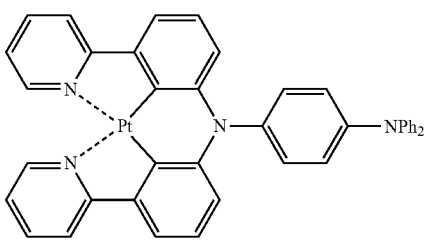
D32
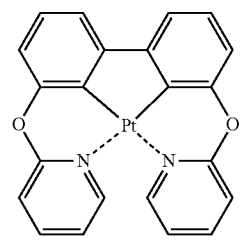
D33
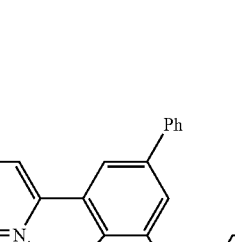
D34
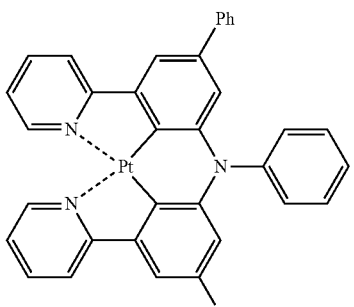
D35
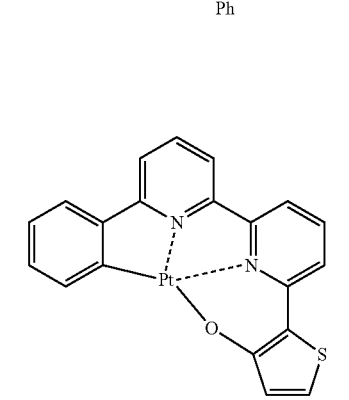
D36

-continued
D37
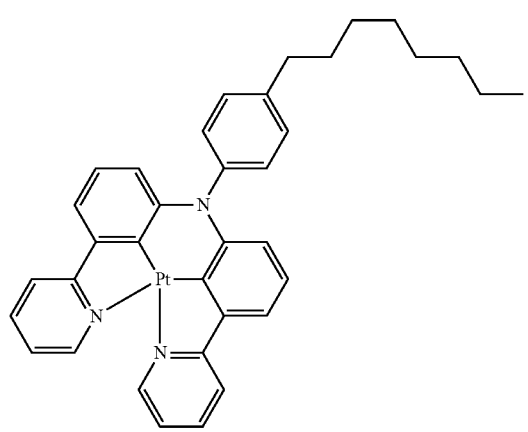
D38
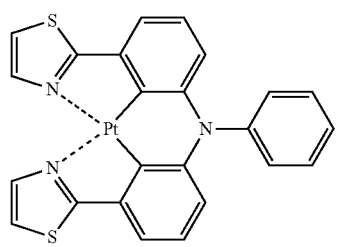
D39
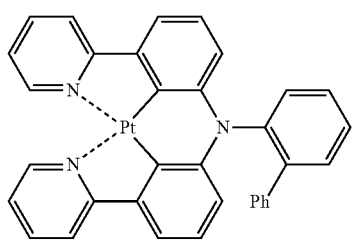
D40
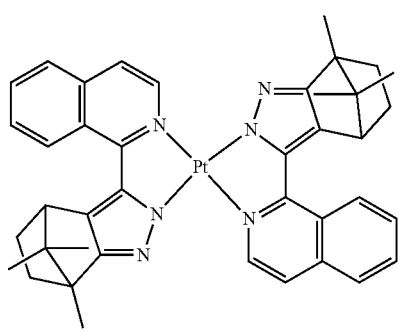
D41
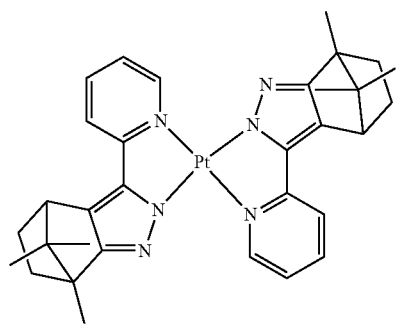
-continued
D42
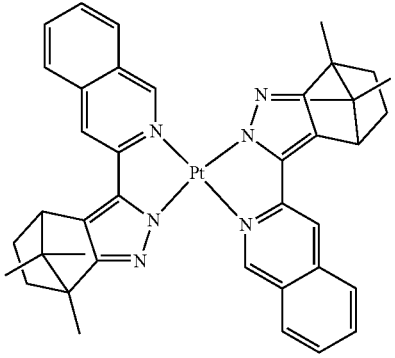
D43
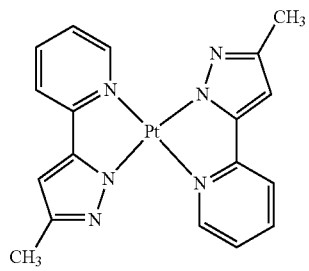
D44
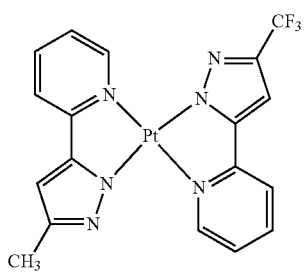
D45
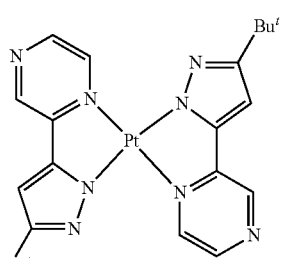
D46
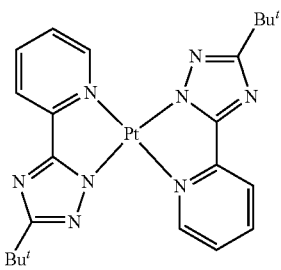

-continued

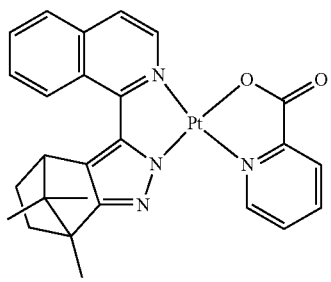
D47

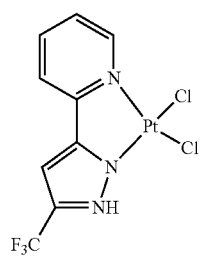
D48

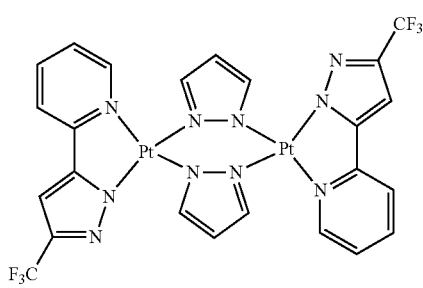
D49

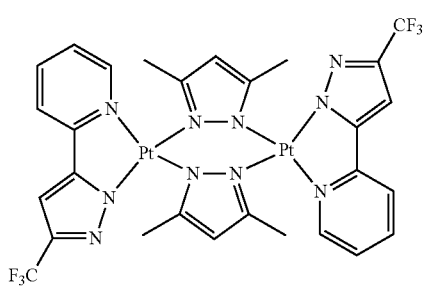
D50

-continued

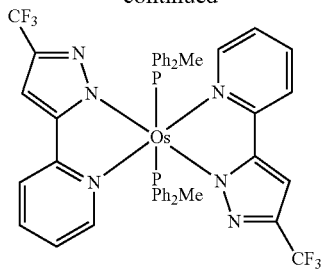
Os(fppz)$_2$(PPh$_2$Me)$_2$

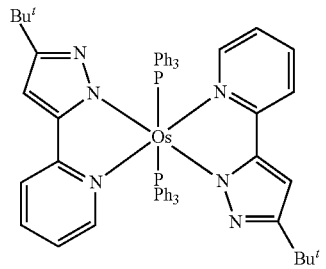
Os(bppz)$_2$(PPh$_3$)$_2$

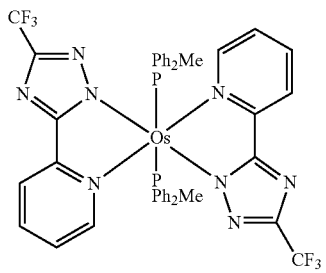
Os(fptz)$_2$(PPh$_2$Me)$_2$

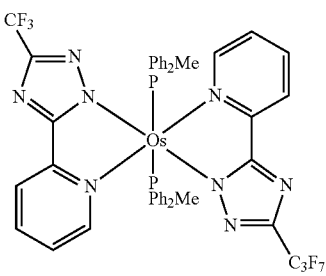
Os(hptz)$_2$(PPhMe$_2$)$_2$

Non-limiting examples of the dopant that may be used in the EML may be Os complexes represented by the following formulae.

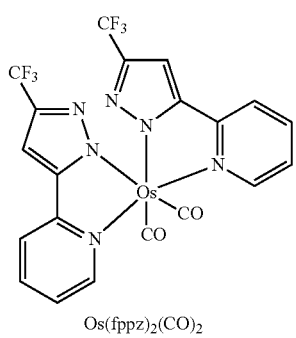
Os(fppz)$_2$(CO)$_2$

When the EML includes both a host and a dopant, the amount of the dopant may be from about 0.01 to about 15 parts by weight based on 100 parts by weight of the host. However, the amount of the dopant is not limited to this range.

The thickness of the EML may be from about 100 Å to about 1000 Å, and in some embodiments, from about 200 Å to about 600 Å. When the thickness of the EML is within these ranges, the EML may have good light emitting ability without a substantial increase in driving voltage.

Then, an ETL may be formed on the EML by vacuum deposition, spin coating, casting, or the like. When the ETL is formed using vacuum deposition or spin coating, the deposition and coating conditions may be similar to those for the formation of the HIL, though the deposition and coating conditions may vary according to a compound that is used to form the ETL. A material for forming the ETL may be the organic compound of Formula 1 above or any known material that can stably transport electrons injected from an electron injecting electrode (cathode). Non-limiting examples of materials for forming the ETL may be a quinoline derivative, such as tris(8-quinolinorate)aluminum (Alq3), TAZ, BAlq, beryllium bis(benzoquinolin-10-olate (Bebq$_2$), 9,10-di (naphthalene-2-yl)anthracene (ADN), BCP, Compound 201, and Compound 202, but are not limited thereto.

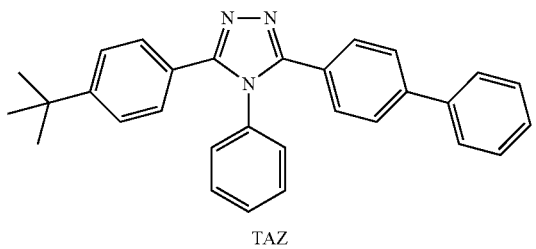

TAZ

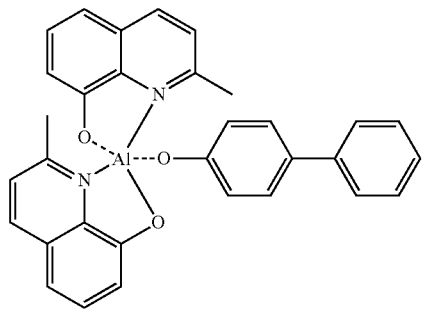

BAlq

Compound 201

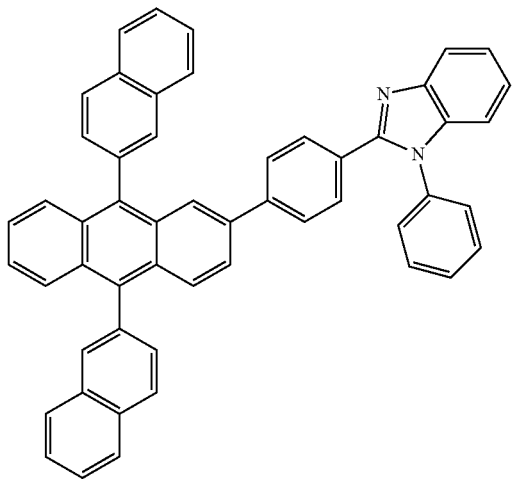

Compound 202

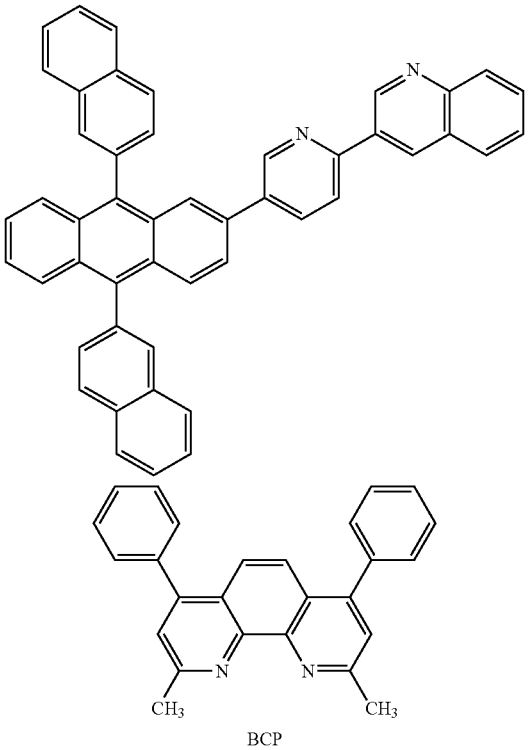

BCP

The thickness of the ETL may be from about 100 Å to about 1000 Å, and in some embodiments, from about 150 Å to about 500 Å. When the thickness of the ETL is within these ranges, the ETL may have satisfactory electron transporting ability without a substantial increase in driving voltage.

In some embodiments, the ETL may further include a metal-containing material, in addition to any known electron-transporting organic compound.

The metal-containing material may include a lithium (Li) complex. Non-limiting examples of the Li complex may be lithium quinolate (LiQ) and Compound 203 below:

Compound 203

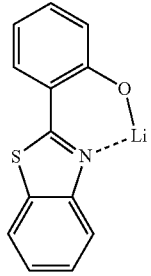

Then, an EIL, which facilitates injection of electrons from the cathode, may be formed on the ETL. Any suitable electron-injecting material may be used to form the EIL.

Non-limiting examples of materials for forming the EIL may be LiF, NaCl, CsF, Li$_2$O, and BaO, which are known in the art. The deposition and coating conditions for forming the EIL may be similar to those for the formation of the HIL, though the deposition and coating conditions may vary according to the material that is used to form the EIL.

The thickness of the EIL may be from about 1 Å to about 100 Å, and in some embodiments, from about 3 Å to about 90 Å. When the thickness of the EIL is within these ranges, the EIL may have satisfactory electron injection ability without a substantial increase in driving voltage.

Finally, the second electrode is disposed on the organic layer. The second electrode may be a cathode that is an electron injection electrode. A material for forming the second electrode may be a metal, an alloy, an electro-conductive compound, which have a low work function, or a mixture thereof. In this regard, the second electrode may be formed of lithium (Li), magnesium (Mg), aluminum (Al), aluminum (Al)-lithium (Li), calcium (Ca), magnesium (Mg)-indium (In), magnesium (Mg)-silver (Ag), or the like, and may be formed as a thin film type transmission electrode. In some embodiments, to manufacture a top-emission light-emitting device, the transmission electrode may be formed of indium tin oxide (ITO) or indium zinc oxide (IZO).

Although the organic light-emitting device of FIG. 1 is described above, the present invention is not limited thereto.

When a phosphorescent dopant is used in the EML, a hole blocking layer (HBL) may be formed between the HTL and the EML or between the H-functional layer and the EML by using vacuum deposition, spin coating, casting, Langmuir-Blodgett (LB) deposition, or the like, in order to prevent diffusion of triplet excitons or holes into the ETL. When the HBL is formed using vacuum deposition or spin coating, the conditions for deposition and coating may be similar to those for the formation of the HIL, although the conditions for deposition and coating may vary according to the material that is used to form the HBL. Any known hole-blocking material may be used. Non-limiting examples of hole-blocking materials may be oxadiazole derivatives, triazole derivatives, and phenanthroline derivatives. For example, bathocuproine (BCP) represented by the following formula may be used as a material for forming the HBL.

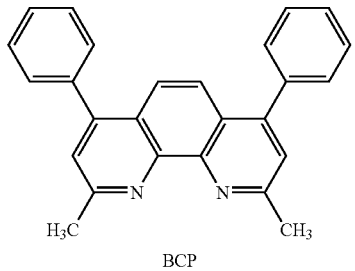

BCP

The thickness of the HBL may be from about 20 Å to about 1000 Å, and in some embodiments, from about 30 Å to about 300 Å. When the thickness of the HBL is within these ranges, the HBL may have improved hole blocking ability without a substantial increase in driving voltage.

According to embodiments of the present invention, the organic light-emitting device may be included in various types of flat panel display devices, such as in a passive matrix organic light-emitting display device or in an active matrix organic light-emitting display device. In particular, when the organic light-emitting device is included in an active matrix organic light-emitting display device including a thin-film transistor, the first electrode on the substrate may function as a pixel electrode, electrically connected to a source electrode or a drain electrode of the thin-film transistor. Moreover, the organic light-emitting device may also be included in flat panel display devices having double-sided screens.

In some embodiments, the organic layer of the organic light-emitting device may be formed of the organic compound of Formula 1 by using a deposition method or may be formed using a wet method of coating a solution of the organic compound of Formula 1.

Hereinafter, the present invention will be described in detail with reference to the following synthesis examples and other examples. However, these examples are for illustrative purposes only and are not intended to limit the scope of the present invention.

EXAMPLES

Synthesis Example 1

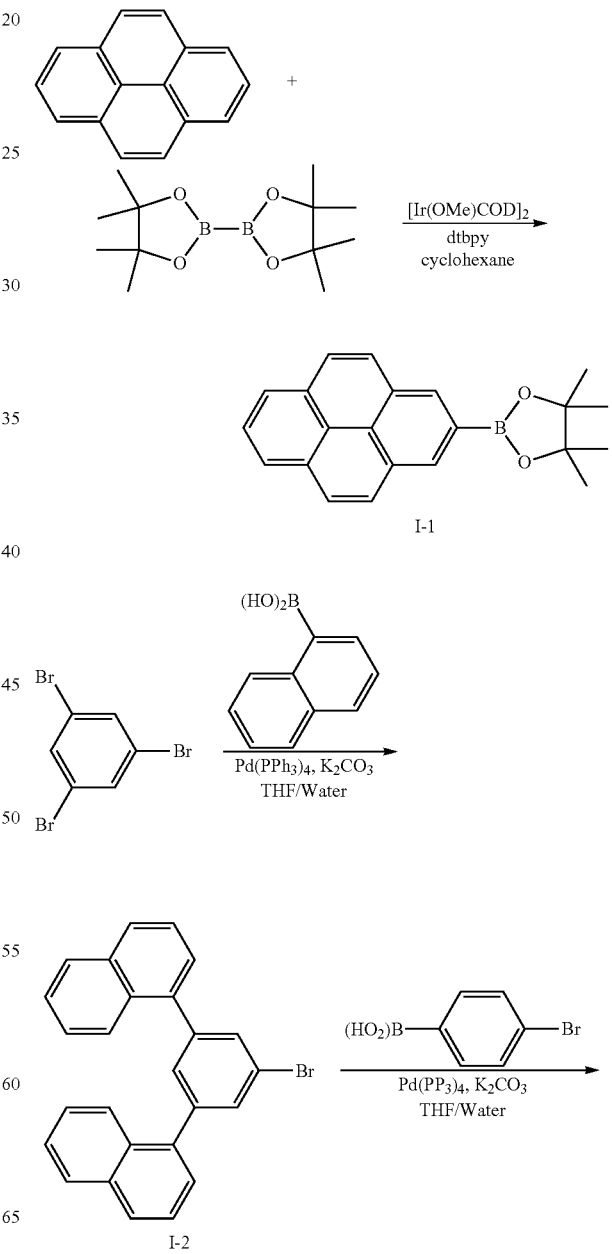

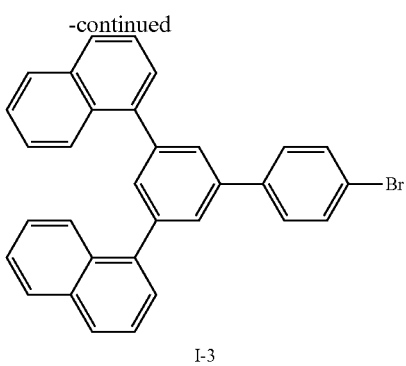

I-3

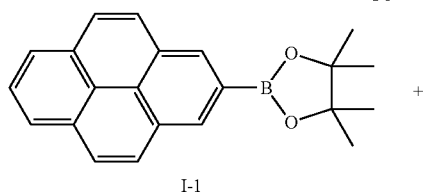

I-1

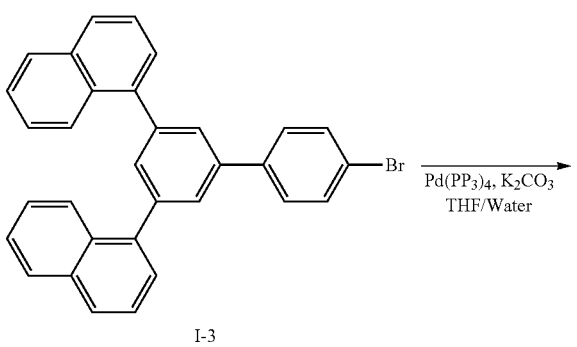

I-3

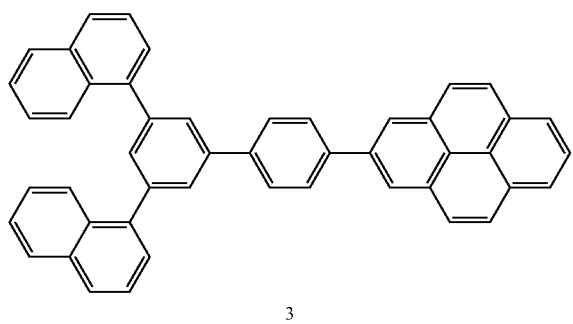

3

Synthesis of Intermediate I-1

4.04 g (20.0 mmol) of pyrene, 5.59 g (22.0 mmol) of bis(pinacolato)diboron, 0.66 g (1.0 mmol) of 1,5-cyclooctadiene)(methoxy)iridium(I) dimmer ([Ir(OMe)COD]$_2$), and 0.54 g (2.0 mmol) of 4,4'-di-tert-butyl-2,2'-bipyridine (dtbpy) were mixed together in 80 mL of cyclohexane, and stirred at about 80° C. for about 24 hours. After the resulting mixture was cooled to room temperature, the solvent was evaporated from the mixture. The residue was separated and purified using silica gel column chlomatography to obtain Intermediate I-1 (4.26 g, Yield: 65%).

Synthesis of Intermediate I-2

3.1 g (10 mmol) of 1,3,5-tribromobenzene, 3.4 g (20 mmol) of naphthalene-1-ylboronic acid, 0.58 g (0.5 mmol) of Pd(PPh$_3$)$_4$, and 4.1 g (30.0 mmol) of K$_2$CO$_3$ were dissolved in 30 mL of a mixed solvent of THF/H$_2$O (2:1 by volume), and stirred at about 80° C. for about 5 hours. After the reaction solution was cooled to room, the reaction solution was added with 40 mL or water and extracted three times with 50 mL of ethylether. The organic layer was collected, and dried using magnesium sulfate to evaporate the solvent. The residue was separated and purified using silica gel column chromatography to obtain 2.7 g of Intermediate I-2 (Yield: 67%). This compound was identified using liquid chromatography-mass spectroscopy (LC-MS). C$_{26}$H$_{17}$Br M$^+$ 409.1

Synthesis of Intermediate I-3

2 g (5.0 mmol) of Intermediate I-2, 1.1 g (5.5 mmol) of 4-bromophenylboronic acid, 0.3 g (0.25 mmol) of Pd(PPh$_3$)$_4$, and 2.1 g (15.0 mmol) of K$_2$CO$_3$ were dissolved in a mixed solvent of THF/H$_2$O (2:1 by volume), and stirred at about 80° C. for about 5 hours. The reaction solution was cooled to room temperature, and then extracted three times with 30 mL of water and 30 mL of diethylether. The organic layer was collected, and dried using magnesium sulfate to evaporate the solvent. The residue was separated and purified using silica gel column chromatography to obtain 1.5 g of Intermediate I-3 (Yield: 62%). This compound was identified using LC-MS. C$_{32}$H$_{21}$Br M$^+$ 485.1

Synthesis of Compound 3

1.8 g (5.5 mmol) of Intermediate I-1, 1.1 g (5.0 mmol) of Intermediate I-3, 0.3 g (0.25 mmol) of Pd(PPh$_3$)$_4$, and 2.1 g (15.0 mmol) of K$_2$CO$_3$ were dissolved in 40 mL of a mixed solvent of THF/H$_2$O (2:1 by volume), and stirred at about 80° C. for about 5 hours. The reaction solution was cooled to room temperature, and then extracted three times with 30 mL of water and 30 mL of diethylether. The organic layer was collected, and dried using magnesium sulfate to evaporate the solvent. The residue was separated and purified using silica gel column chromatography to obtain 2.03 g of Compound 3 (Yield: 67%). This compound was identified using mass spectroscopy/fast atom bombardment (MS/FAB) and $^1$H nuclear magnetic resonance (NMR). C$_{48}$H$_{30}$ cal. 606.23. found 607.35.

δ=8.29 (d, 2H), 8.23-8.21 (ss, 2H), 8.09-8.06 (ss, 2H), 8.05-8.01 (m, 1H), 7.95-7.94 (t, 1H), 7.90-7.81 (m, 12H), 7.76-7.74 (m, 2H), 7.54-7.51 (m, 2H), 7.40-7.38 (m, 2H), 7.25-7.21 (m, 2H), 7.16-7.13 (m, 2H)

Intermediate:

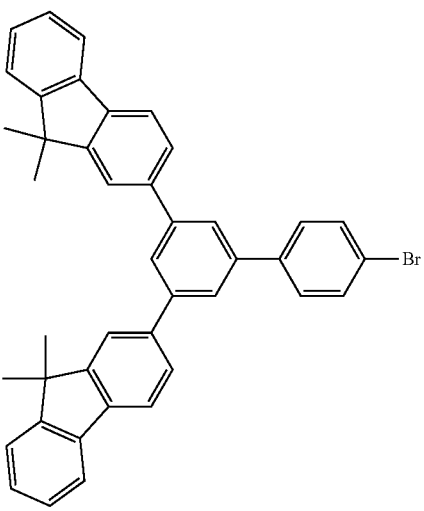

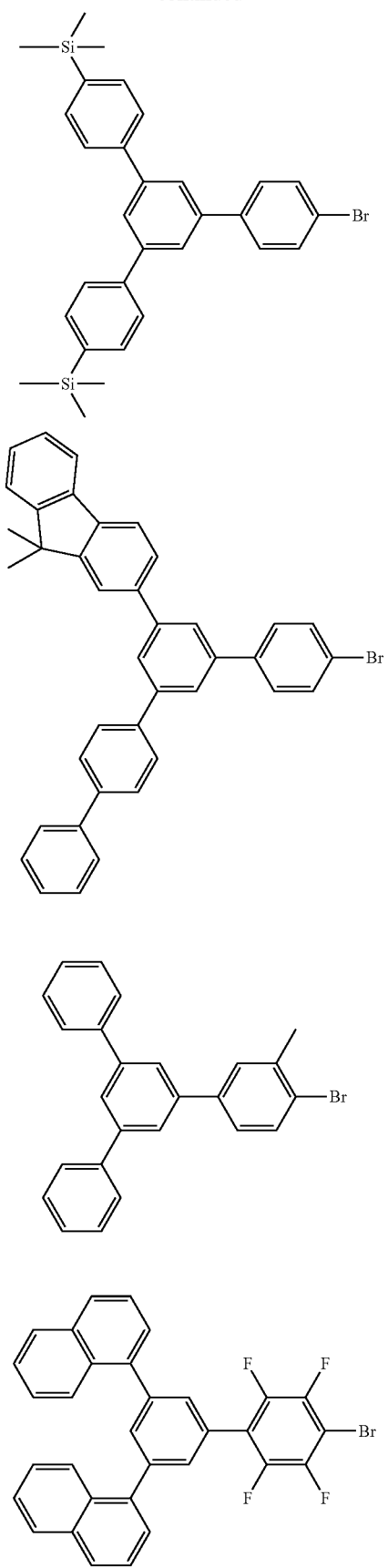
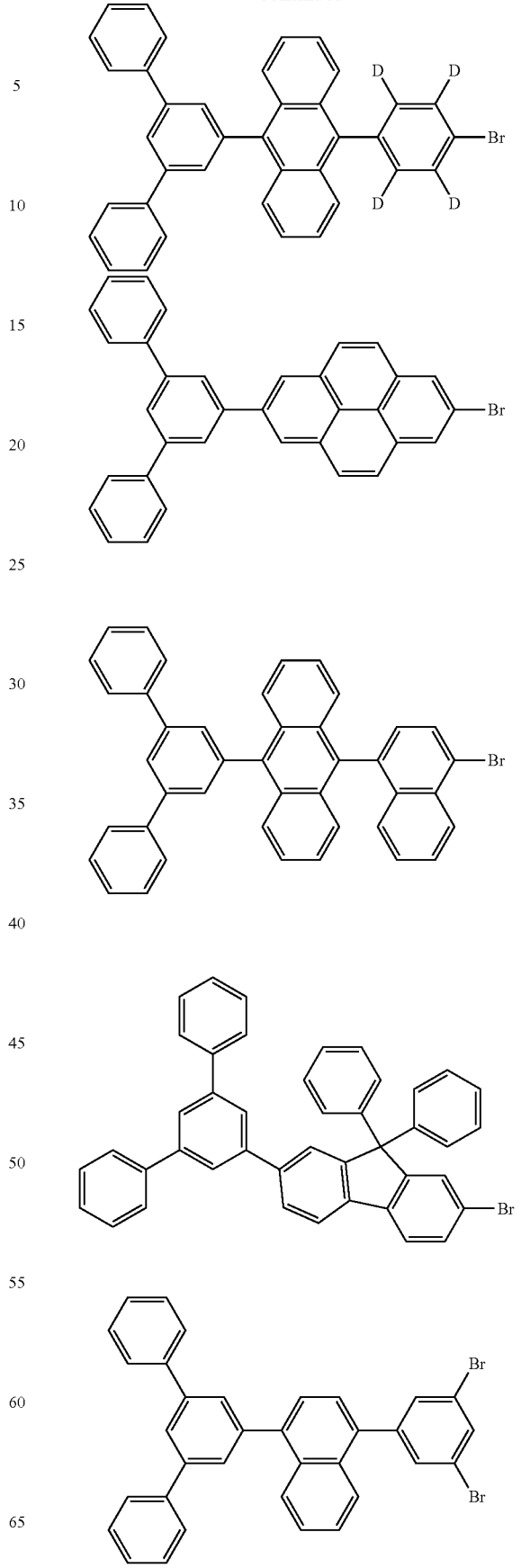

-continued

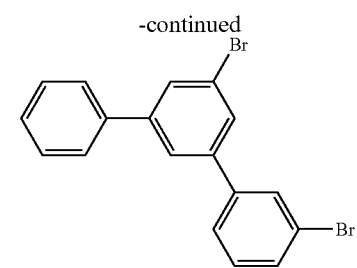
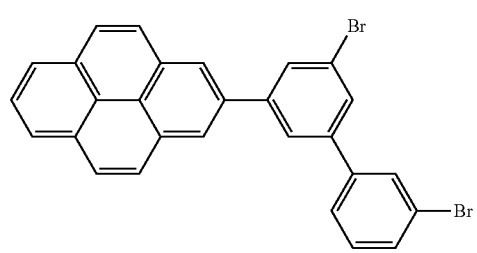
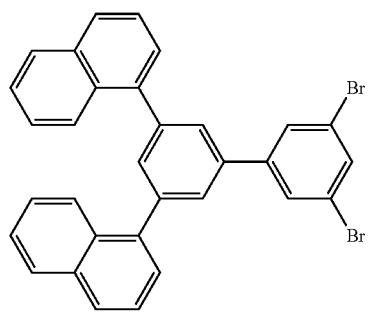
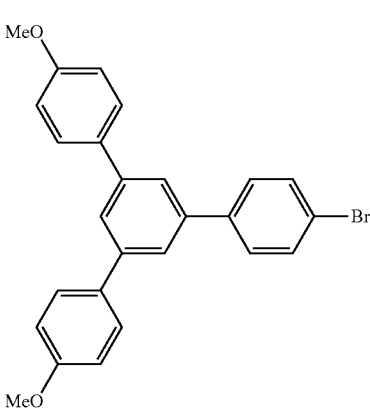

-continued

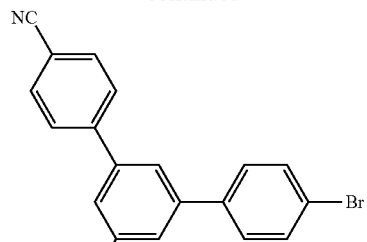
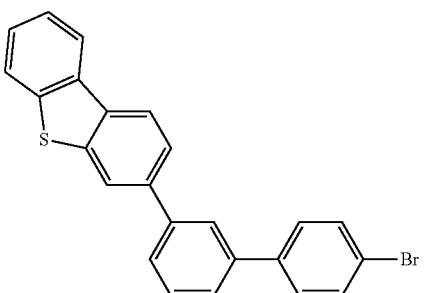
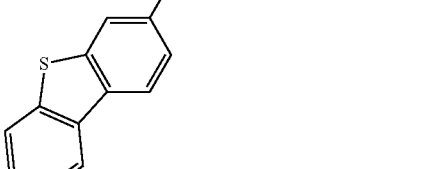
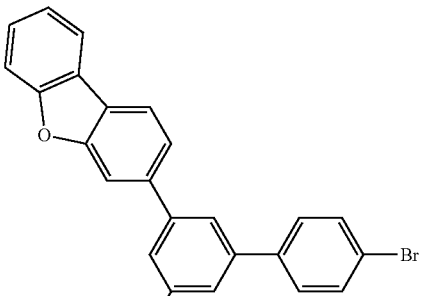

Additional compounds were synthesized using appropriate intermediate materials according to the synthetic pathways and the methods described as above, and were identified using $^1$H NMR and MS/FAB. The results are shown in Table 1 below.

Synthetic pathways and source materials for other compounds not in Table 1 will be obvious to one of ordinary skill in the art based on the synthetic pathways and source materials described above.

TABLE 1

| | ¹H NMR (CDCl₃, 400 MHz) | MS/FAB found | MS/FAB calc. |
|---|---|---|---|
| 3 | δ = 8.29 (d, 2H), 8.23-8.21 (ss, 2H), 8.09-8.06 (ss, 2H), 8.05-8.01 (m, 1H), 7.95-7.94 (t, 1H), 7.90-7.81 (m, 12H), 7.76-7.74 (m, 2H), 7.54-7.51 (m, 2H), 7.40-7.38 (m, 2H), 7.25-7.21 (m, 2H), 7.16-7.13 (m, 2H) | 607.35 | 606.23 |
| 7 | δ = 8.29 (s, 2H), 8.23-8.21 (ss, 2H), 8.09 (s, 1H), 8.06 (s, 1H), 8.05 (s, 1H), 7.90-7.87 (m, 3H), 7.81-7.79 (m, 5H), 7.74 (s, 1H), 7.72 (s, 1H), 7.69 (d, 1H), 7.62-7.61 (t, 1H), 7.55-7.52 (dd, 2H), 7.35-7.31 (m, 2H), 7.29-7.28 (d, 2H), 7.15-7.09 (m, 4H), 1.57 (s, 12H) | 739.37 | 738.33 |
| 10 | δ = 8.29 (m, 2H), 8.23-8.21 (m, 2H), 8.09-8.06 (m, 3H), 7.90-7.78 (m, 1H), 7.87-7.86 (m, 1H), 7.83-7.78 (m, 4H), 7.69-7.67 (m, 6H), 7.64-7.63 (m, 1H), 7.60-7.57 (m, 4H), 0.36-0.35 (s, 18H) | 651.31 | 650.28 |
| 15 | δ = 8.29 (s, 2H), 8.23-8.21 (ss, 2H), 8.09 (s, 1H), 8.06 (s, 1H), 8.05 (s, 1H), 7.90-7.87 (m, 2H), 7.83 (s, 1H), 7.81-7.79 (m, 4H), 7.76-7.73 (m, 4H), 7.70 (m, 2H), 7.67 (m, 2H), 7.61-7.58 (m, 2H), 7.55 (d, 1H), 7.53-7.49 (m, 2H), 7.42-7.40 (m, 1H), 7.33 (d, 1H), 7.29 (d, 1H), 7.16-7.09 (m, 2H), 1.57 (s, 12H) | 699.33 | 698.30 |
| 16 | δ = 8.23 (s, 1H), 8.21 (s, 1H), 8.09 (s, 1H), 8.05-8.01 (m, 1H), 7.88 (m, 2H), 7.79 (s, 1H), 7.77 (s, 1H), 7.73 (m, 2H), 7.68-7.63 (m, 5H), 7.60 (d, 2H), 7.52-7.51 (m, 2H), 7.49-7.39 (m, 5H), 2.21 (m, 3H) | 521.46 | 520.22 |
| 18 | δ = 8.23-8.21 (m, 4H), 8.18 (m, 2H), 8.14 (s, 1H), 8.12 (s, 1H), 8.10-8.08 (m, 2H), 8.06-8.01 (m, 2H), 7.92-7.90 (m, 2H), 7.83-7.81 (m, 4H), 7.76-7.74 (m, 2H), 7.54-7.51 (m, 2H), 7.25-7.21 (m, 2H), 7.16-7.13 (m, 2H) | 679.37 | 678.20 |
| 20 | δ = 8.29 (m, 2H), 8.23-8.21 (ss, 2H), 8.09 (s, 1H), 8.06 (s, 1H), 8.05 (s, 1H), 7.94-7.93 (d, 2H), 7.85-7.81 (m, 4H), 7.76-7.72 (m, 5H), 7.58-7.56 (m, 2H), 7.49-7.39 (m, 6H), 7.38-7.36 (dd, 2H), 7.32-7.28 (m, dH) | 687.54 | 686.29 |
| 21 | δ = 8.49 (m, 2H), 8.46-8.45 (m, 4H), 8.23 (s, 1H), 8.21 (s, 1H), 8.09 (s, 1H), 8.06 (s, 1H), 8.05-8.01 (m, 1H), 8.00 (m, 4H), 7.92 (s, 1H), 7.90 (s, 1H), 7.79-7.78 (d, 2H), 7.76-7.75 (m, 1H), 7.68-7.66 (m, 4H), 7.49-7.39 (m, 6H) | 631.42 | 630.23 |
| 24 | δ = 8.32 (m, 2H), 8.23 (s, 1H), 8.21 (s, 1H), 8.14-8.11 (m, 1H), 8.09-8.01 (m, 3H), 7.94-7.90 (m, 5H), 7.83-7.80 (m, 2H), 7.75-7.72 (m, 5H), 7.67-7.65 (m, 2H), 7.57-7.54 (m, 2H), 7.49-7.40 (m, 7H), 7.32-7.25 (m, 3H), 7.20-7.16 (m, 1H), 7.01-6.97 (m, 1H) | 733.35 | 732.28 |
| 27 | δ = 8.23-8.21 (m, 4H), 8.09 (s, 1H), 8.06 (s, 1H), 8.05-8.01 (m, 1H), 7.94-7.92 (dd, 1H), 7.87-7.84 (m, 3H), 7.74 (t, 1H), 7.69-7.65 (m, 6H), 7.61-7.55 (m, 2H), 7.49-7.39 (m, 6H), 7.27-7.25 (m, 4H), 7.18-7.17 (m, 2H), 7.15-7.06 (m, 6H) | 747.43 | 746.30 |
| 32 | δ = 8.49 (s, 4H), 8.23-8.21 (ss, 4H), 8.09-8.06 (ss, 2H), 8.05-8.01 (m, 4H), 7.97-7.96 (m, 4H), 7.88 (m, 4H), 7.84-7.83 (d, 3H), 7.72-7.69 (m, 7H), 7.49-7.40 (m, 6H), 6.98-6.91 (m, 2H) | 833.46 | 832.31 |
| 33 | δ = 8.49 (m, 2H), 8.37 (m, 2H), 8.23 (m, 2H), 8.21 (m, 2H), 8.09 (s, 2H), 8.06 (s, 2H), 8.05-8.01 (m, 2H), 7.94-7.92 (m, 2H), 7.90 (s, 1H), 7.86 (s, 1H), 7.82-7.77 (m, 4H), 7.70-7.66 (m, 4H), 7.49-7.39 (m, 3H), 7.24-7.20 (m, 1H) | 631.43 | 630.23 |
| 34 | δ = 8.49 (m, 4H), 8.37 (m, 2H), 8.23-8.21 (ss, 6H), 8.09 (s, 2H), 8.06 (s, 2H), 8.05-8.01 (m, 3H), 7.94-7.92 (m, 3H), 7.86-7.84 (m, 10H), 7.70-7.66 (m, 2H), 7.24-7.20 (m, 1H) | 755.45 | 754.27 |
| 38 | δ = 8.49 (s, 4H), 8.23-8.21 (ss, 4H), 8.09 (s, 2H), 8.06 (s, 2H), 8.05-8.00 (m, 3H), 7.94-7.90 (m, 9H), 7.87 (d, 2H), 7.83-7.74 (m, 4H), 7.54-7.51 (m, 2H), 7.40-7.38 (m, 2H), 7.25-7.21 (m, 2H), 7.16-7.13 (m, 2H) | 807.42 | 806.30 |
| 41 | δ = 8.29 (s, 2H), 8.23-8.21 (ss, 2H), 8.09 (s, 1H), 8.06 (s, 1H), 8.05-8.01 (m, 1H), 7.90-7.86 (m, 2H), 7.83-7.78 (m, 4H), 7.69-7.68 (d, 2H), 7.65 (m, 1H), 7.60-7.58 (m, 4H), 7.00-6.98 (m, 4H), 3.84 (s, 6H) | 567.45 | 566.22 |
| 42 | δ = 8.29 (m, 2H), 8.23-8.21 (m, 2H), 8.09 (s, 1H), 8.06 (s, 1H), 8.05-8.01 (s, 1H), 7.90-7.86 (m, 3H), 7.83 (s, 1H), 7.81-7.78 (m, 7H), 7.76-7.75 (m, 2H), 7.70-7.67 (m, 4H) | 557.44 | 556.19 |
| 43 | δ = 8.34 (m, 1H), 8.32 (m, 1H), 8.29 (m, 2H), 8.23 (s, 1H), 8.21 (s, 1H), 8.17 (m, 2H), 8.10-8.01 (m, 5H), 7.90-7.78 (m, 10H), 7.75 (d, 2H), 7.73-7.71 (t, 1H), 7.46-7.42 (m, 2H), 7.38-7.34 (m, 2H) | 719.23 | 718.18 |
| 44 | δ = 8.29 (m, 2H), 8.23-8.21 (ss, 2H), 8.09 (s, 1H), 8.06 (s, 1H), 8.05-8.00 (m, 3H), 7.97-7.95 (m, 2H), 7.90-7.86 (m, 2H), 7.83 (m, 1H), 7.81-7.78 (m, 3H), 7.73-7.66 (m, 9H), 7.54-7.51 (m, 2H), 7.45-7.41 (m, 2H) | 687.40 | 686.22 |

Example 1

To manufacture an anode, a corning 15 Ω/cm2 (1200 Å) ITO glass substrate was cut to a size of 50 mm×50 mm×0.7 mm and then sonicated in isopropyl alcohol and pure water each for five minutes, and then cleaned by irradiation of ultraviolet rays for 30 minutes and exposure to ozone. The resulting glass substrate was loaded into a vacuum deposition device.

A widely known material 4,4',4"-Tris(N-(2-naphthyl)-N-phenyl-amino)-triphenylamine (hereinafter, "2-TNATA") was vacuum-deposited on a surface of the substrate to form a HIL having a thickness of about 600 Å, and then 4,4'-bis[N-(1-naphthyl)-N-phenylamino]biphenyl (hereinafter, "NPB") as a known hole transporting compound was vacuum-deposited to form a HTL having a thickness of about 300 Å.

Afterward, the organic Compound 3 of Formula 1 as a blue fluorescent host, and 4,4'-bis[2-(4-(N,N-diphenylamino)phenyl)vinyl]biphenyl (hereinafter, "DPAVBi") as a known blue fluorescent dopant were co-deposited in a weight ratio of 98:2 on the HTL to form an EML having a thickness of about 300 Å.

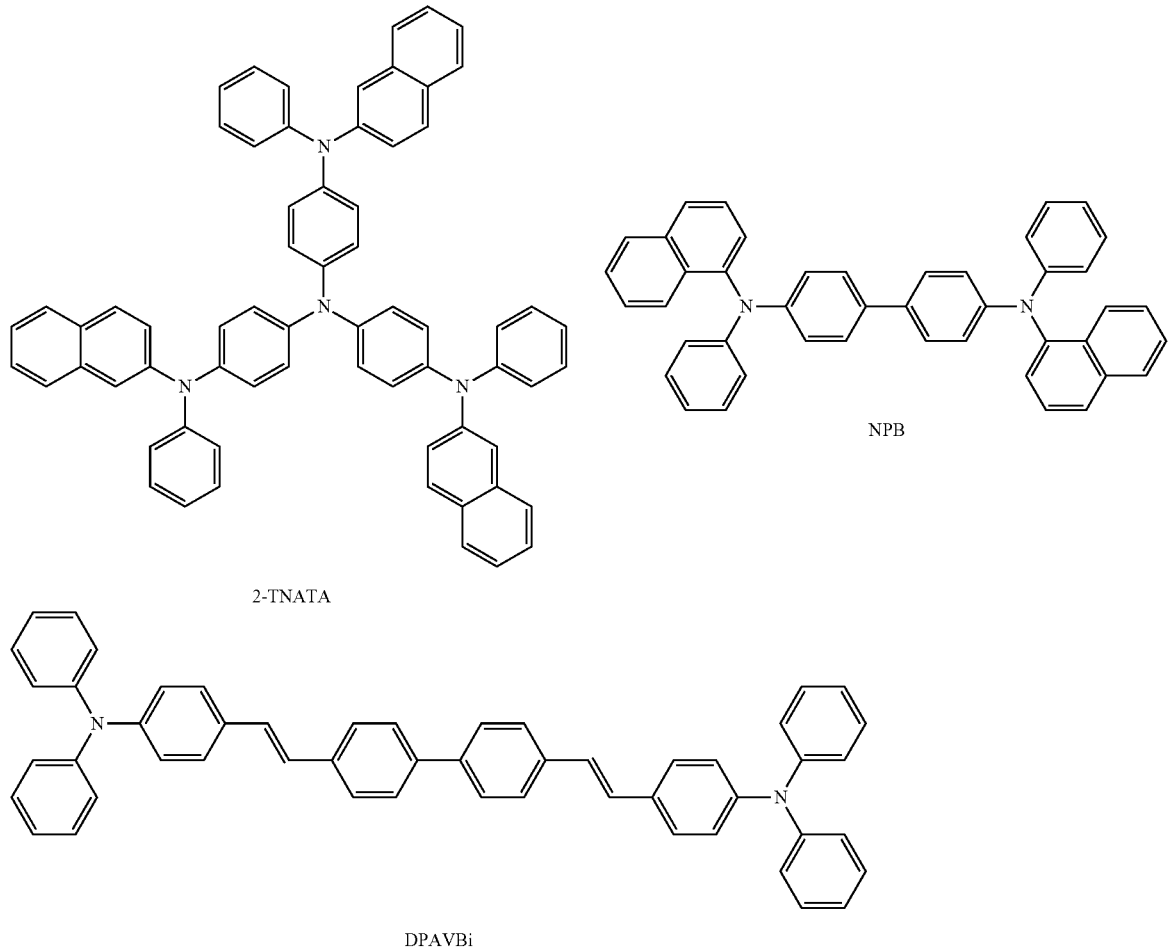

2-TNATA

NPB

DPAVBi

Then, Alq$_3$ was deposited on the EML to form an ETL having a thickness of 300 Å, and then LiF, which is a halogenated alkali metal, was deposited on the ETL to form an EIL having a thickness of 10 Å. Then, Al was vacuum-deposited on the EIL to form a cathode having a thickness of 3000 Å, thereby forming a LiF/Al electrode and completing the manufacture of an organic light-emitting device.

The organic light-emitting device had a driving voltage of about 6.21V at a current density of 50 mA/cm$^2$, a luminosity of 3,040 cd/m$^2$, a luminescent efficiency of 6.08 cd/A, and a half life-span (hr @ 100 mA/cm$^2$) of about 302 hours.

Example 2

An organic light-emitting device was manufactured in the same manner as in Example 1, except that Compound 20, instead of Compound 3, was used to form the EML.

The organic light-emitting device had a driving voltage of about 6.38V at a current density of 50 mA/cm$^2$, a luminosity of 3,060 cd/m$^2$, a luminescent efficiency of 6.12 cd/A, and a half life-span (hr @ 100 mA/cm$^2$) of about 276 hours.

Example 3

An organic light-emitting device was manufactured in the same manner as in Example 1, except that Compound 24, instead of Compound 3, was used to form the EML.

The organic light-emitting device had a driving voltage of about 6.29V at a current density of 50 mA/cm$^2$, a luminosity of 3,205 cd/m$^2$, a luminescent efficiency of 6.41 cd/A, and a half life-span (hr @ 100 mA/cm$^2$) of about 322 hours.

Example 4

An organic light-emitting device was manufactured in the same manner as in Example 1, except that Compound 27 was used, instead of Compound 3, to form the EML.

The organic light-emitting device had a driving voltage of about 6.25V at a current density of 50 mA/cm², a luminosity of 3,135 cd/m², a luminescent efficiency of 6.27 cd/A, and a half life-span (hr @ 100 mA/cm²) of about 317 hours.

Example 5

An organic light-emitting device was manufactured in the same manner as in Example 1, except that Compound 40 was used, instead of Compound 3, to form the EML.

The organic light-emitting device had a driving voltage of about 6.36V at a current density of 50 mA/cm², a luminosity of 3,190 cd/m², a luminescent efficiency of 6.38 cd/A, and a half life-span (hr @ 100 mA/cm²) of about 337 hours.

Example 6

An organic light-emitting device was manufactured in the same manner as in Example 1, except that Compound 42 was used, instead of Compound 3, to form the EML.

The organic light-emitting device had a driving voltage of about 6.33V at a current density of 50 mA/cm², a luminosity of 3,130 cd/m², a luminescent efficiency of 6.26 cd/A, and a half life-span (hr @ 100 mA/cm²) of about 319 hours.

Comparative Example 1

An organic light-emitting device was manufactured in the same manner as in Example 1, except that a widely known blue fluorescent host 9,10-di-naphthalene-2-yl-anthracene (DNA) was used, instead of Compound 3, to form the EML.

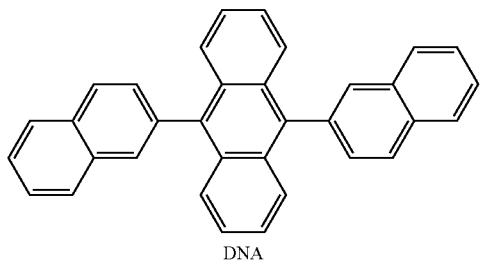 [SMILES: c1ccc2cc(-c3c4ccccc4c(-c4ccc5ccccc5c4)c4ccccc34)ccc2c1]

DNA

The organic light-emitting device had a driving voltage of about 7.35V at a current density of 50 mA/cm², a luminosity of 2.065 cd/m², a luminescent efficiency of 4.13 cd/A, and a half life-span (hr @ 100 mA/cm²) of about 145 hours.

The organic light-emitting devices manufactured using the organic compounds represented by Formula 1 according to embodiments as host materials for blue EML had lower driving voltages and improved I-V-L characteristics with a higher efficiency, as compared to those manufactured using a widely-known material DNA. In particular, the organic light-emitting devices according to the embodiments had markedly improved lifetimes. The characteristics of the organic light-emitting devices of Examples 1-6 and Comparative Example 1 are shown in Table 2 below.

TABLE 2

|  | Light-emitting material | Driving voltage (V) | Current density (mA/cm²) | Luminance (cd/m²) | Efficiency (cd/A) | Emission color | Half-life span (hr @100 mA/cm²) |
|---|---|---|---|---|---|---|---|
| Example 1 | Compound 3 | 6.21 | 50 | 3,040 | 6.08 | Blue | 302 hr |
| Example 2 | Compound 20 | 6.38 | 50 | 3,060 | 6.12 | Blue | 276 hr |
| Example 3 | Compound 24 | 6.29 | 50 | 3,205 | 6.41 | Blue | 322 hr |
| Example 4 | Compound 27 | 6.25 | 50 | 3,135 | 6.27 | Blue | 317 hr |
| Example 5 | Compound 40 | 6.36 | 50 | 3,190 | 6.38 | Blue | 337 hr |
| Example 6 | Compound 42 | 6.33 | 50 | 3,130 | 6.26 | Blue | 319 hr |
| Comparative Example 1 | DNA | 7.35 | 50 | 2,065 | 4.13 | Blue | 145 hr |

The organic compound of Formula 1 above has improved light-emitting capability, and thus is suitable as a light-emitting material for fluorescent or phosphorescent devices of any color, such as red, green, blue, and white fluorescent and phosphorescent devices. Therefore, organic light-emitting devices having high efficiency, low driving voltages, high luminance, and long lifetime may be manufactured using the organic compound of Formula 1.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. An organic compound represented by Formula 1 below:

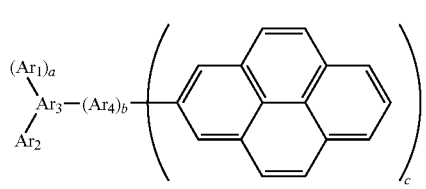

Formula 1 wherein $Ar_1$, $Ar_2$, and $Ar_4$ are each independently a substituted or unsubstituted $C_6$-$C_{60}$ aryl group, a substituted or unsubstituted $C_{10}$-$C_{60}$ condensed polycyclic group, or a substituted or unsubstituted $C_3$-$C_{60}$ heteroaryl group;

Ar$_3$ is a group represented by Formula 3a or Formula 3b below:

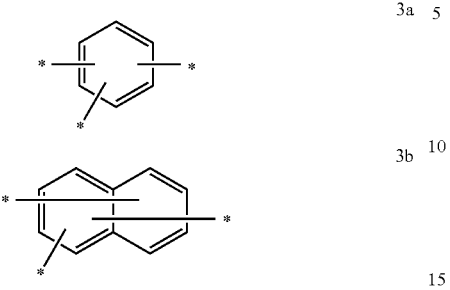

wherein, in Formula 3a and 3b, * indicates a binding site;
a is an integer from 0 to 2;
b is an integer from 0 to 4; and
c is an integer from 1 to 3, wherein b is optionally at least two, and the two or more Ar$_4$s are identical to or differ from each other.

2. The organic compound of claim 1, wherein Ar$_1$ and Ar$_2$ are each independently a compound represented by one of Formulae 2a to 2e:

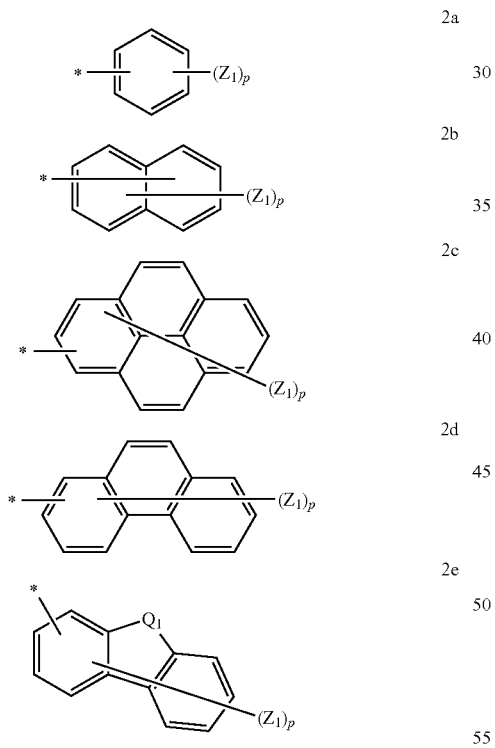

wherein Q$_1$ is a linker represented by —C(R$_{30}$)(R$_{31}$)—, —N(R$_{32}$)—, —S—, or —O—;
Z$_1$, R$_{30}$, R$_{31}$, and R$_{32}$ are each independently hydrogen, deuterium, a substituted or unsubstituted C$_1$-C$_{20}$ alkyl group, a substituted or unsubstituted C$_5$-C$_{20}$ aryl group, a substituted or unsubstituted C$_3$-C$_{20}$ heteroaryl group, a substituted or unsubstituted C$_6$-C$_{20}$ condensed polycyclic group, —Si(R$_{40}$)$_3$, a halogen group, a cyano group, a nitro group, a hydroxy group, or a carboxy group;
R$_{40}$ is a substituted or unsubstituted C$_1$-C$_{20}$ alkyl group, a substituted or unsubstituted C$_5$-C$_{20}$ aryl group, a substituted or unsubstituted C$_3$-C$_{20}$ heteroaryl group, or a substituted or unsubstituted C$_6$-C$_{20}$ condensed polycyclic group;
p is an integer from 1 to 9; and
* indicates a binding site.

3. The organic compound of claim 1, wherein, in Formula 1, Ar$_4$ is a group represented by one of Formulae 4a to 4f:

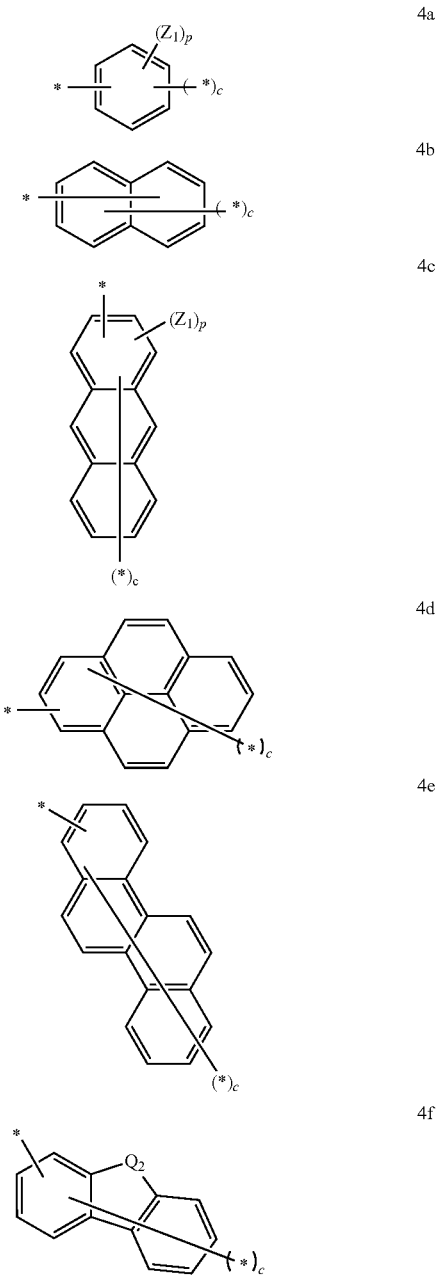

wherein Q$_2$ is a linker represented by —C(R$_{30}$)(R$_{31}$)—;
Z$_1$, R$_{30}$, and R$_{31}$ are each independently hydrogen, deuterium, a substituted or unsubstituted C$_1$-C$_{20}$ alkyl group, a substituted or unsubstituted C$_5$-C$_{20}$ aryl group, a substituted or unsubstituted C$_3$-C$_{20}$ heteroaryl group, a substituted or unsubstituted C$_6$-C$_{20}$ condensed polycyclic group, a halogen group, a cyano group, a nitro group, a hydroxyl group, or a carboxy group; and p is an integer from 1 to 9;

c is an integer from 1 to 3; and

* indicates a binding site.

4. The organic compound of claim 1, wherein the compound of Formula 1 is one of the compounds below:

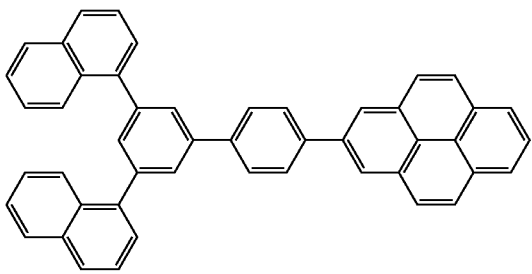

3

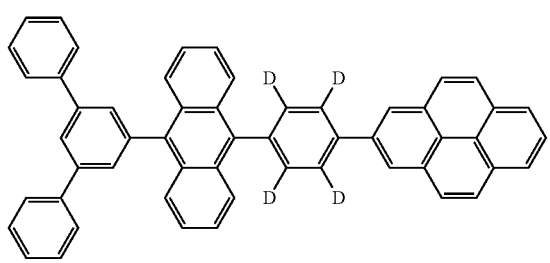

20

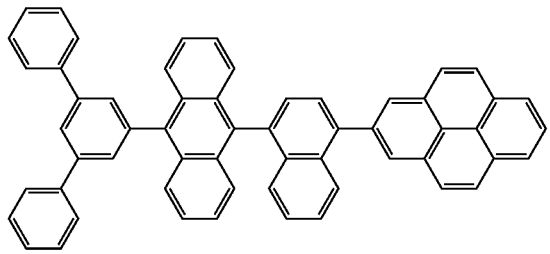

24

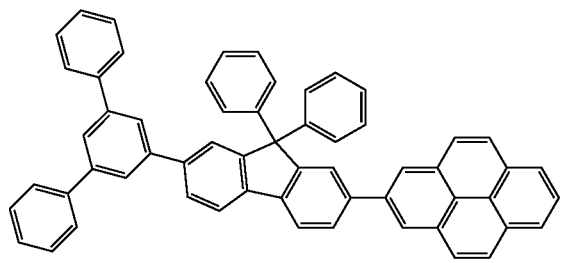

27

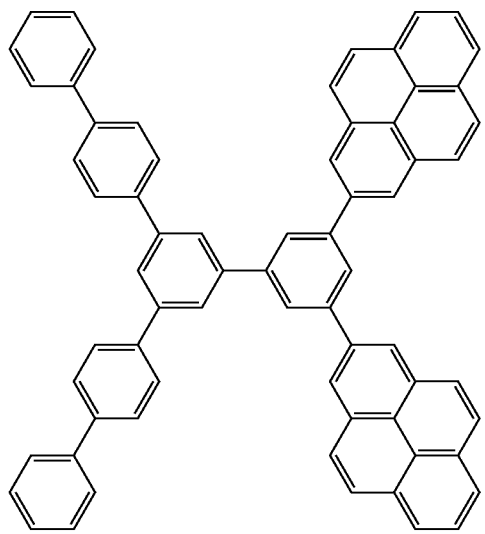

40

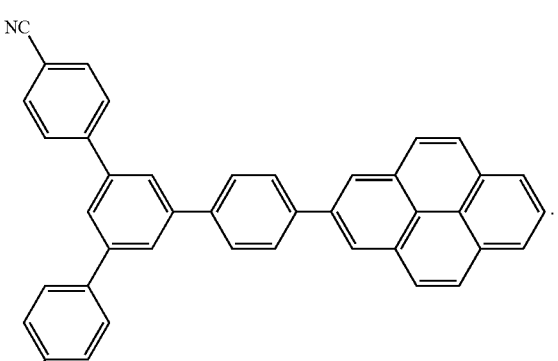

42

5. An organic light-emitting device comprising:
a first electrode;
a second electrode; and
an organic layer interposed between the first electrode and the second electrode, wherein the organic layer comprises the organic compound of claim 1.

6. The organic light-emitting device of claim 5, wherein the organic layer comprises an emission layer.

7. The organic light-emitting device of claim 5, wherein the organic layer comprises a blue emission layer.

8. The organic light-emitting device of claim 5, wherein the organic layer comprises an emission layer, a hole injection layer, a hole transport layer, or a functional layer having both hole injection and hole transport capabilities;
the emission layer comprises the organic compound represented by Formula 1 below:

Formula 1

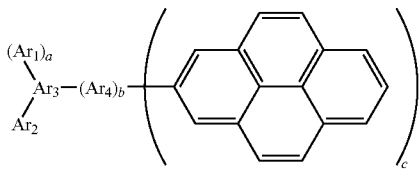

wherein $Ar_1$, $Ar_2$, and $Ar_4$ are each independently a substituted or unsubstituted $C_6$-$C_{60}$ aryl group, a substituted or unsubstituted $C_{10}$-$C_{60}$ condensed polycyclic group, or a substituted or unsubstituted $C_3$-$C_{60}$ heteroaryl group;

$Ar_3$ is a group represented by Formula 3a or Formula 3b below:

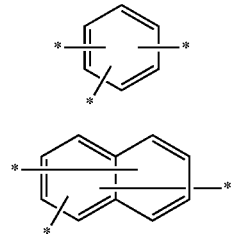

3a

3b wherein, in Formula 3a and 3b, * indicates a binding site;
a is an integer from 0 to 2;
b is an integer from 0 to 4; and
c is an integer from 1 to 3, wherein b is optionally at least two, and the two or more $Ar_4$s are identical to or differ from each other.

9. The organic light-emitting device of claim 8, wherein the emission layer further comprises an anthracene-based compound, an arylamine-based compound, or a styryl-based compound.

10. The organic light-emitting device of claim 8, wherein the emission layer comprises red, green, blue, and white emission layers, and one of which comprises a phosphorescent compound.

11. The organic light-emitting device of claim 8, wherein at least one of the hole injection layer, the hole transport layer, and the functional layer having both hole injection and hole transport capabilities comprises a charge-generating material.

12. The organic light-emitting device of claim 11, wherein the charge-generating material is a p-type dopant.

13. The organic light-emitting device of claim 12, wherein the p-type dopant is a quinine derivative; a metal oxide; or a cyano group-containing compound.

14. The organic light-emitting device of claim 5, wherein the organic layer comprises an electron transport layer, and the electron transport layer comprises an electron transporting organic compound and a metal complex.

15. The organic light-emitting device of claim 14, wherein the metal complex is a Li complex.

16. The organic light-emitting device of claim 14, wherein the metal complex is lithium quinolate (LiQ), or Compound 203 below

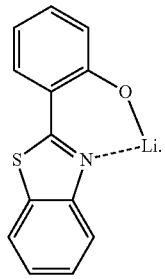

Compound 203

17. The organic light-emitting device of claim 5, wherein the organic layer is formed from the organic compound represented by Formula 1 below using a wet process:

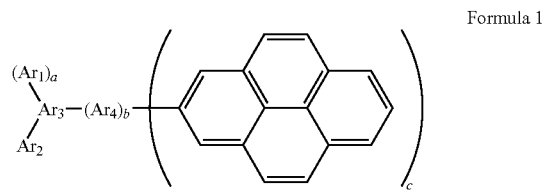

Formula 1 wherein $Ar_1$, $Ar_2$, and $Ar_4$ are each independently a substituted or unsubstituted $C_6$-$C_{60}$ aryl group, a substituted or unsubstituted $C_{10}$-$C_{60}$ condensed polycyclic group, or a substituted or unsubstituted $C_3$-$C_{60}$ heteroaryl group;

$Ar_3$ is a group represented by Formula 3a or Formula 3b below:

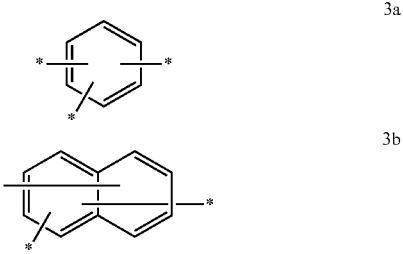

3a

3b wherein, in Formula 3a and 3b, * indicates a binding site;
a is an integer from 0 to 2;
b is an integer from 0 to 4; and
c is an integer from 1 to 3, wherein b is optionally at least two, and the two or more $Ar_4$s are identical to or differ from each other.

18. A flat panel display device comprising the organic light-emitting device of claim 5, wherein the first electrode of the organic light-emitting device is electrically connected to a source electrode or a drain electrode of a thin-film transistor.

* * * * *